(12) United States Patent
Ohyama et al.

(10) Patent No.: US 11,694,659 B2
(45) Date of Patent: Jul. 4, 2023

(54) DISPLAY APPARATUS, IMAGE PROCESSING APPARATUS, AND CONTROL METHOD

(71) Applicant: Panasonic Intellectual Property Management Co., Ltd., Osaka (JP)

(72) Inventors: Tatsushi Ohyama, Osaka (JP); Mariko Miyashita, Hyogo (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

(21) Appl. No.: 17/120,085

(22) Filed: Dec. 11, 2020

(65) Prior Publication Data
US 2021/0097961 A1   Apr. 1, 2021

Related U.S. Application Data
(63) Continuation of application No. PCT/JP2019/024410, filed on Jun. 20, 2019.

(30) Foreign Application Priority Data

Jul. 11, 2018  (JP) ................ 2018-131681
Jun. 10, 2019  (JP) ................ 2019-108042

(51) Int. Cl.
*G09G 5/377* (2006.01)
*G09G 5/02* (2006.01)
(Continued)

(52) U.S. Cl.
CPC ......... *G09G 5/377* (2013.01); *G01N 21/6456* (2013.01); *G01N 33/0027* (2013.01);
(Continued)

(58) Field of Classification Search
CPC .... G09G 5/377; G09G 5/02; G09G 2340/125; G01N 21/6456; G01N 33/0027;
(Continued)

(56) References Cited

U.S. PATENT DOCUMENTS

| 2002/0118352 A1 | 8/2002 | Ohzu et al. |
| 2005/0069207 A1* | 3/2005 | Zakrzewski .......... G06K 9/629 |
| | | 382/218 |

(Continued)

FOREIGN PATENT DOCUMENTS

| JP | 7-190879 | 7/1995 |
| JP | 2002-250769 | 9/2002 |

(Continued)

OTHER PUBLICATIONS

Shahraiyni et al. "Monitoring of dust storm and estimation of aerosol concentration in the Middle East using remotely sensed images", Jan. 9, 2014, Saudi Society for Geosciences (Year: 2014).*

(Continued)

*Primary Examiner* — YuJang Tswei
(74) *Attorney, Agent, or Firm* — McDermott Will & Emery LLP

(57) ABSTRACT

A display apparatus includes a display screen, and a controller that causes the display screen to display a composite image in which a first image acquired by imaging a space by a camera and a second image representing at least one type of aerosol existing in the space are combined. The position of the at least one type of aerosol as seen in a depth direction in the first image is reflected in the second image.

21 Claims, 19 Drawing Sheets

(51) Int. Cl.

| | | |
|---|---|---|
| *G06T 17/00* | (2006.01) | |
| *G01N 21/64* | (2006.01) | |
| *G01N 33/00* | (2006.01) | |
| *G01S 17/89* | (2020.01) | |
| *G01N 15/00* | (2006.01) | |
| *G01S 7/51* | (2006.01) | |
| *G01N 21/47* | (2006.01) | |
| *G06T 19/20* | (2011.01) | |
| *G01N 21/53* | (2006.01) | |
| *G01N 21/17* | (2006.01) | |
| *G01S 17/86* | (2020.01) | |
| *G01N 15/06* | (2006.01) | |
| *G06T 19/00* | (2011.01) | |
| *G01S 7/48* | (2006.01) | |
| *G06F 3/147* | (2006.01) | |

(52) U.S. Cl.
CPC .............. *G01S 17/89* (2013.01); *G06T 17/00* (2013.01); *G09G 5/02* (2013.01); *G01N 15/06* (2013.01); *G01N 21/53* (2013.01); *G01N 2015/0046* (2013.01); *G01N 2015/0693* (2013.01); *G01N 2021/1793* (2013.01); *G01N 2021/4792* (2013.01); *G01N 2201/0631* (2013.01); *G01S 7/4802* (2013.01); *G01S 7/51* (2013.01); *G01S 17/86* (2020.01); *G06F 3/147* (2013.01); *G06T 19/006* (2013.01); *G06T 19/20* (2013.01); *G06T 2219/004* (2013.01); *G06T 2219/2012* (2013.01); *G09G 2340/125* (2013.01)

(58) Field of Classification Search
CPC ........... G01N 2201/0631; G01N 15/06; G01N 2015/0693; G01N 21/53; G01N 2015/0046; G01N 2021/1793; G01N 2021/4792; G01S 17/89; G01S 7/4802; G01S 7/51; G01S 17/86; G06T 17/00; G06T 19/20; G06T 2219/004; G06T 2219/2012; G06T 19/006; G06F 3/147
See application file for complete search history.

(56) References Cited

U.S. PATENT DOCUMENTS

| | | | | |
|---|---|---|---|---|
| 2007/0211018 | A1* | 9/2007 | Kaga | G09F 9/37 345/107 |
| 2010/0332474 | A1* | 12/2010 | Birdwell | G06F 16/285 707/E17.089 |
| 2012/0326993 | A1* | 12/2012 | Weisman | G06F 9/453 345/173 |
| 2013/0057687 | A1 | 3/2013 | Ehlgen et al. | |
| 2013/0215132 | A1* | 8/2013 | Fong | G06F 3/011 345/582 |
| 2013/0242301 | A1* | 9/2013 | Berg | G01N 15/1434 356/336 |
| 2013/0302746 | A1* | 11/2013 | Liang | A61B 5/4547 433/29 |
| 2014/0037194 | A1* | 2/2014 | Kitamura | G06T 7/344 382/154 |
| 2015/0253844 | A1* | 9/2015 | Ueno | G06T 19/00 345/419 |
| 2017/0030706 | A1 | 2/2017 | Natori et al. | |
| 2017/0038290 | A1 | 2/2017 | Nakai et al. | |
| 2017/0089800 | A1 | 3/2017 | Huseynov et al. | |
| 2017/0351241 | A1* | 12/2017 | Bowers | G06N 5/022 |
| 2018/0042583 | A1* | 2/2018 | Pringle | H01J 49/164 |
| 2018/0147658 | A1* | 5/2018 | Shapiro | B23K 26/364 |
| 2018/0192881 | A1* | 7/2018 | Endo | G02B 21/367 |
| 2018/0217042 | A1 | 8/2018 | Jongerius et al. | |
| 2018/0284015 | A1 | 10/2018 | Imade et al. | |
| 2019/0156563 | A1* | 5/2019 | Wada | G06T 15/80 |
| 2019/0335073 | A1 | 10/2019 | Yamashita et al. | |
| 2019/0361995 | A1* | 11/2019 | Facon | G06Q 30/0601 |
| 2021/0287451 | A1* | 9/2021 | Baudisch | G06F 30/00 |

FOREIGN PATENT DOCUMENTS

| | | |
|---|---|---|
| JP | 2003-294567 | 10/2003 |
| JP | 2005-502056 | 1/2005 |
| JP | 2007-232374 | 9/2007 |
| JP | 2007-525648 | 9/2007 |
| JP | 2007-303855 | 11/2007 |
| JP | 2013-521481 | 6/2013 |
| JP | 2013-210990 A | 10/2013 |
| JP | 2014-206291 | 10/2014 |
| JP | 2014-528090 | 10/2014 |
| JP | 2015-135291 | 7/2015 |
| JP | 2017-032362 | 2/2017 |
| JP | 2018-521315 | 8/2018 |
| WO | 2003/021291 | 3/2003 |
| WO | 2005/029046 | 3/2005 |
| WO | 2013/052062 | 4/2013 |
| WO | 2015/156037 A1 | 10/2015 |
| WO | 2016/181854 | 11/2016 |
| WO | 2018/061816 | 4/2018 |
| WO | 2019/138641 | 7/2019 |

OTHER PUBLICATIONS

International Search Report of PCT application No. PCT/JP2019/024410 dated Sep. 10, 2019.

\* cited by examiner

FIG. 4

| Data No. i | SENSOR DATA | | | | | REFERENCE SENSOR POSITION | | |
|---|---|---|---|---|---|---|---|---|
| | SUBSTANCE NAME Mi | DENSITY Di | DISTANCE ri | HORIZONTAL ANGLE φi | VERTICAL ANGLE θi | x0 | y0 | z0 |
| 1 | POLLEN | 200 | 50 | 30 | 10 | 0 | 0 | 50 |
| 2 | DUST | 50 | 100 | 30 | 10 | 0 | 0 | 50 |
| ... | ... | ... | ... | ... | ... | ... | ... | ... |

FIG. 5

| CONTROL LEVEL Ci | CONDITIONAL EXPRESSION |
| --- | --- |
| 1 | $D_i < L_m \times 0.4$ |
| 2 | $L_m \times 0.4 \leq D_i < L_m \times 0.7$ |
| 3 | $L_m \times 0.7 \leq D_i < L_m \times 1.2$ |
| 4 | $L_m \times 1.2 \leq D_i < L_m \times 1.4$ |
| 5 | $L_m \times 1.4 \leq D_i$ |

FIG. 6

| SUBSTANCE NAME Mm | REFERENCE VALUE Lm |
| --- | --- |
| POLLEN | 100 |
| DUST | 500 |
| $CO_2$ | 1000 |
| MOISTURE | 100 |
| SURFACE ORGANIC DIRT | 10 |

| SUBSTANCE NAME Mm | REPRESENTATIVE VALUE Cm OF CONTROL LEVEL |
|---|---|
| POLLEN | 5 |
| DUST | 5 |
| $CO_2$ | 3 |
| MOISTURE | 1 |
| SURFACE ORGANIC DIRT | 5 |
| AVERAGE | 3.8 |

FIG. 13

| Data No. i | SUBSTANCE NAME Mi | DENSITY Di | CONTROL LEVEL Ci | SPACE COORDINATE | | |
|---|---|---|---|---|---|---|
| | | | | Xi | Yi | Zi |
| 1 | POLLEN | 200 | 5 | 150 | 20 | 50 |
| 2 | DUST | 50 | 2 | 100 | 70 | 0 |
| ... | ... | ... | ... | ... | ... | ... |

FIG. 22
(a)
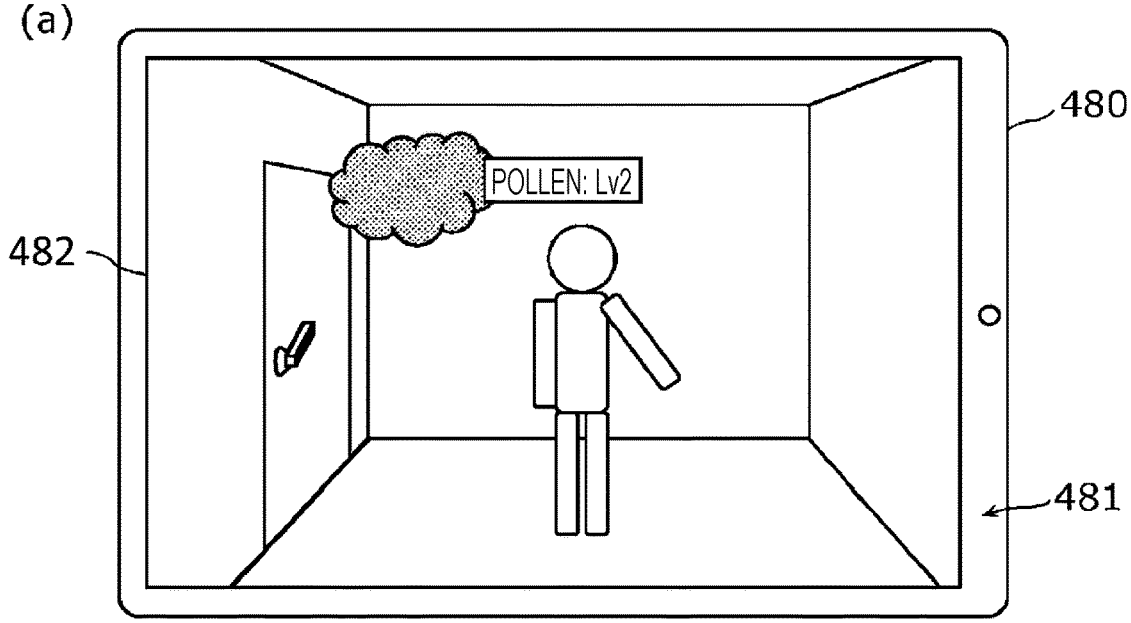
(b)
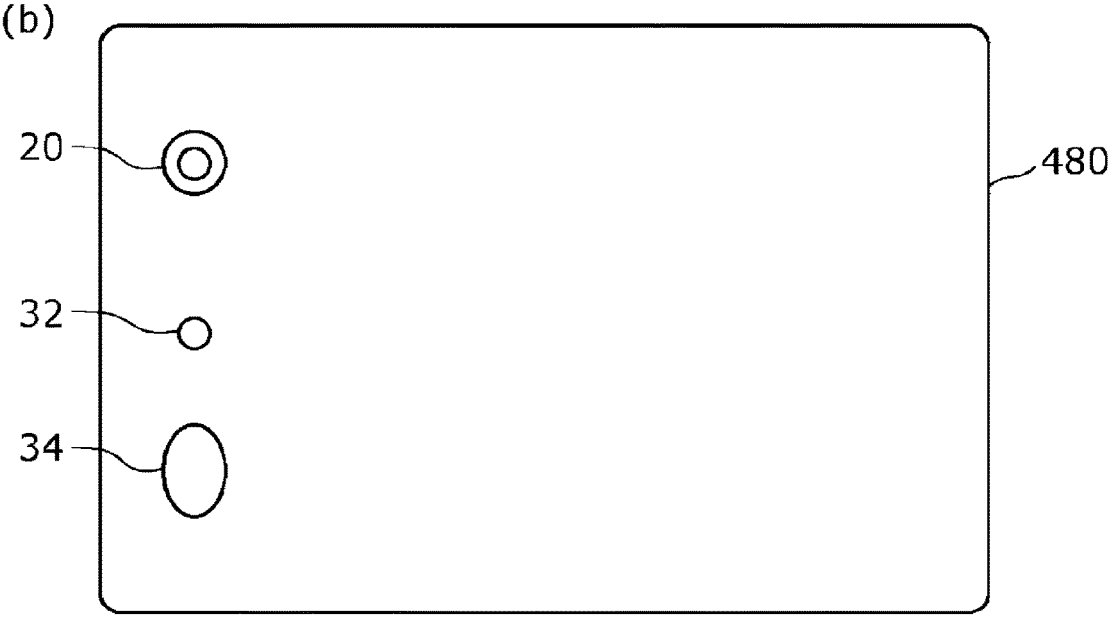

DISPLAY APPARATUS, IMAGE PROCESSING APPARATUS, AND CONTROL METHOD

BACKGROUND

1. Technical Field

The present disclosure relates to a display apparatus, an image processing apparatus, and a control method.

2. Description of the Related Art

A terminal apparatus is known that visually displays a substance that floats in the air, such as pollen or dust, in the form of aerosol. For example, such terminal apparatuses are disclosed in Japanese Unexamined Patent Application Publication No. 2014-206291 and International Publication No. 2016/181854.

SUMMARY

In one general aspect, the techniques disclosed here feature a display apparatus including a display screen, and a controller that causes the display screen to display a composite image in which a first image acquired by imaging a space by a camera and a second image representing at least one type of aerosol existing in the space are combined. The position of the at least one type of aerosol as seen in a depth direction in the first image is reflected in the second image.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 4 is a diagram showing an example of sensor data output from a sensor apparatus according to an embodiment;

FIG. 5 is a block diagram showing a conditional expression for determining a control level in a non-contact sensing system according to an embodiment;

FIG. 6 is a diagram showing an example of a reference value database indicating a reference value for each substance;

FIG. 13 is a diagram showing an example of a 3D database generated by a non-contact sensing system according to an embodiment;

FIG. 22 is a diagram showing a display apparatus integrally provided with a non-contact sensing system according to an embodiment.

DETAILED DESCRIPTION

Overview of the Present Disclosure

Figure 1:
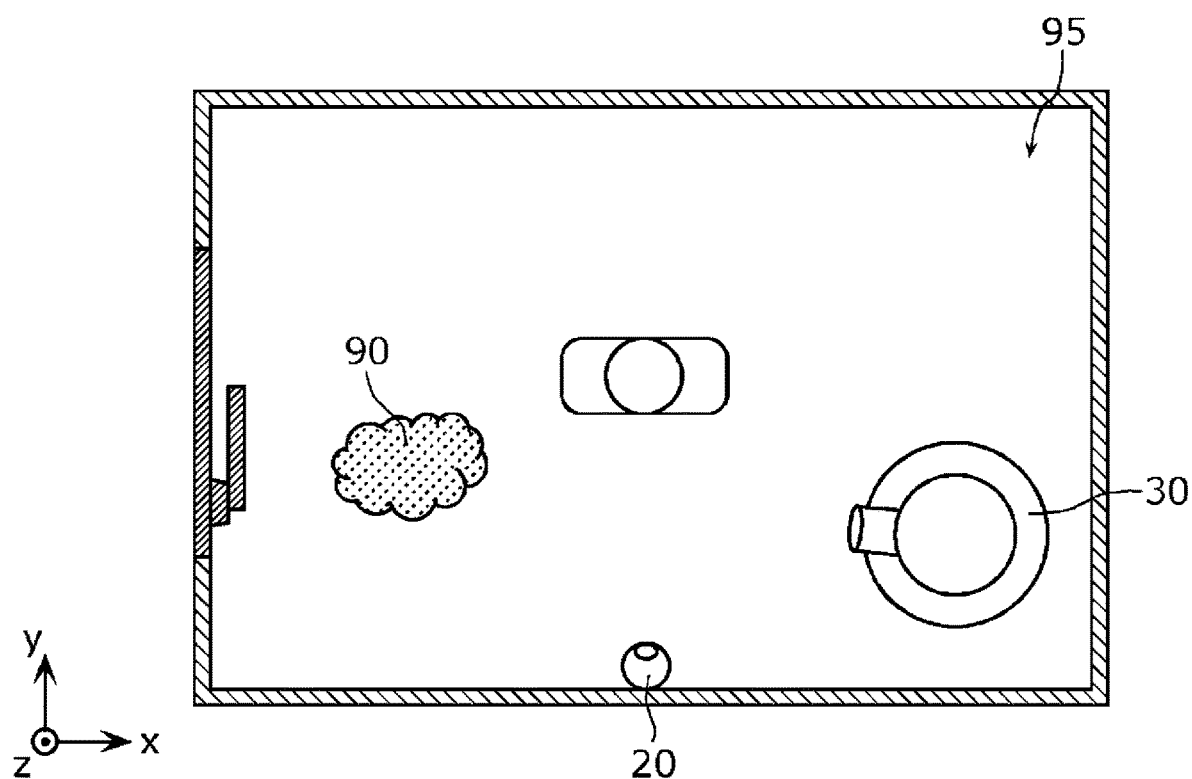
FIG. 1 is a top view showing a space to which a non-contact sensing system according to an embodiment is applied.

In an aspect, the present disclosure provides a display apparatus including a display screen, and a controller that causes the display screen to display a composite image in which a first image acquired by imaging a space by a camera and a second image representing at least one type of aerosol existing in the space are combined. The position of the at least one type of aerosol as seen in a depth direction in the first image is reflected in the second image.

As described above, in the second image representing the aerosol, the position of the aerosol in the depth direction is reflected. That is, not only the position of the aerosol in vertical and horizontal directions represented by the first image but also the position of the aerosol as seen in the depth direction in the first image is displayed on the display screen. Thus, the position of the aerosol is presented with high accuracy.

For example, the first image may represent a two-dimensional space. The controller may generate the second image by projecting three-dimensional coordinate data representing the position of the at least one type of aerosol in the space onto the two-dimensional space. The controller may generate the composite image by combining the first image and the second image.

This allows it to accurately present the position of the aerosol n the two-dimensional space.

For example, the controller may acquire the three-dimensional coordinate data from a sensor that acquires a position of the at least one type of aerosol in the space. The controller may convert the first image into a pseudo three-dimensional image. The controller may generate the second image by projecting the three-dimensional coordinate data into the two-dimensional space such that the pseudo three-dimensional image and the three-dimensional coordinate data correspond to each other.

This allows it to accurately present the position of the aerosol in the pseudo three-dimensional space.

For example, the second image may include a contour representing a boundary of a region in which the at least one type of aerosol exists and distance information representing a distance in the space from a reference position to a representative position of the region inside the contour.

This makes it possible to display the boundary of the region in which the aerosol exists on the display screen, and also the position of the aerosol in the depth direction represented by the representative position. Thus, the position of the aerosol is displayed in a simple fashion that allows a user to easily understand the position by viewing the display screen.

For example, the representative position may be a center of gravity of a density distribution of the at least one type of aerosol in the region inside the contour.

In this case, the representative position can be easily determined by a calculation based on the density distribution. In many cases, the closer to the center of the aerosol, the higher the density, and thus employing the center of gravity of the density distribution as the representative position makes it possible to accurately present the position of the aerosol.

For example, the distance information may be a numerical value indicating the distance.

The numerically displaying of the distance makes it possible to indicate the position of the aerosol in a manner that allows a user to easily understand the position.

For example, the distance information may be a color that is predetermined according to the distance and is applied to the region inside the contour.

This allows a user to distinguish distances by colors, that is, the position of the aerosol is displayed in a manner that allows the user to easily understand the position.

For example, the composite image may represent a three-dimensional model including the space and a contour representing a boundary of a region in which the at least one type of aerosol exists.

By converting the composite image into the three-dimensional model, it becomes possible to display the image as seen from various viewpoints on the display screen. Thus, the position of the aerosol can be displayed in a manner that allows a user to easily understand the position.

For example, the second image may be a moving image including images that are switched as time passes. Each of the images may correspond to a distance from a reference position in the space, and may include a contour indicating a boundary of a region, at the corresponding distance, in which the at least one type of aerosol exists.

Thus, images representing the aerosol at respective distances are sequentially displayed and high-accuracy positions of aerosol are presented.

For example, a density of the at least one type of aerosol may be further reflected in the second image.

This allows it to present not only the position of the aerosol but also the density of the aerosol. As a result, a larger amount of information and more types of information are presented to a user. This makes it possible to more effectively assist in determining whether or not to take measures against the aerosol, such as performing ventilation.

For example, the second image may include level information indicating a density level of the at least one type of aerosol.

By classifying the aerosol densities into levels, it becomes possible to display the aerosol density in a simple manner that allows a user to easily understand the aerosol density by viewing the display screen.

For example, the at least one type of aerosol may include two or more types of aerosol, and the second image may represent the respective two or more types of aerosol in different display modes.

Thus, even when two or more types of aerosol exist, it is possible to display the types in different modes depending on the types.

For example, the controller may further cause the display screen to display an image for warning a user in a case where a density of the at least one type of aerosol is greater than a threshold value.

This can prompt a user to take countermeasures against the aerosol.

In an aspect, the present disclosure provides an image processing apparatus including an acquisition circuit that acquires three-dimensional coordinate data representing a position, in a space, of at least one type of aerosol existing in the space, and a processor. The processor generates a composite image in which a first image acquired by imaging the space by a camera and a second image representing the at least one type of aerosol existing in the space are combined based on the three-dimensional coordinate data. A position of the at least one type of aerosol as seen in a depth direction in the first image is reflected in the second image.

As described above, in the second image representing the aerosol, the position of the aerosol in the depth direction is reflected. That is, not only the position of the aerosol in the vertical and horizontal directions represented by the first image but also the position of the aerosol as seen in the depth direction in the first image is represented in the composite image displayed on the display screen. Thus, when the composite image generated by the image processing apparatus according to the present aspect is displayed on the display screen, the position of aerosol is accurately presented.

According to an aspect, the present disclosure provides a control method of controlling a system, the system including a display apparatus and a sensor including a light source that emits irradiation light toward at least one type of object in a space and a photodetector that detects return light returning from the at least one type of object, the sensor outputting data representing a result of detection of the return light by the photodetector, the control method including acquiring the data from the sensor, generating three-dimensional coordinate data representing a position, in the space, of the at least one type of object based on the data, based on the three-dimensional coordinate data, generating a composite image in which a first image and a second image are combined, the first image being obtained by imaging the space by a camera, the second image representing the at least one type of object existing in the space and reflecting a position of the at least one type of object as seen in a depth direction in the first image, and causing the display apparatus to display the composite image.

As described above, in the second image representing the object, the position of the object in the depth direction is reflected. That is, not only the position of the object in the vertical and horizontal directions represented by the first image but also the position of the object as seen in the depth direction in the first image is displayed on the display screen. Thus, the position of the object is presented with high accuracy.

For example, the return light may be fluorescent light emitted by the at least one type of object by being excited by the irradiation light, and the generating of the composite image may include determining a type of the at least one type of object by analyzing the fluorescent light and reflecting the type in the second image.

This allows it to present not only the position of the object and also the type of the object. As a result, a larger amount of information and more types of information are presented to a user, which makes it possible to assist in determining whether or not to take measures against the object, such as performing ventilation.

For example, the irradiation light may include a polarization component, and the generating of the composite image may include determining the type of the at least one type of object based on a degree of depolarization of the polarization component included in the return light and reflecting the type in the second image.

This allows it to present not only the position of the object and also the type of the object. As a result, a larger amount of information and more types of information are resented to a user, which makes it possible to assist in determining whether or not to take measures against the object, such as performing ventilation or disinfection.

For example, the three-dimensional coordinate data may be generated using coordinates of a position of the sensor in the space and a relative positional relationship between the sensor and the at least one type of object calculated based on a difference between an irradiation light emission time and a return light reception time.

In this case, the detection of the object and the measurement of the distance to the detected object can be performed using the same light source and the same photodetector, and thus the configuration of the sensor apparatus can be simplified.

For example, the at least one type of object may be an organic substance stuck to an object existing in the space.

This makes it possible to detect a substance containing an organic substance such as vomit or pollen and accurately present the position thereof.

For example, the at least one type of object may be aerosol existing in the space.

That is, it is possible to detect a substance floating in the air such as pollen or dust and accurately present the position thereof.

For example, the return light may be backscattered light generated as a result of scattering of the irradiation light by the at least one type of object.

This allows it to accurately detect aerosol.

According to an aspect, the present disclosure provides a non-transitory computer-readable storage medium storing a program for controlling a system, the system including a display apparatus and a sensor including a light source that emits irradiation light toward at least one type of object in a space and a photodetector that detects return light returning from the at least one type of object, the sensor outputting data representing a result of the detection of the return light by the photodetector, the program, when executed by the computer, performing acquiring the data from the sensor, generating three-dimensional coordinate data representing a position, in the space, of the at least one type of object based on the data, based on the three-dimensional coordinate data, generating a composite image in which a first image and a second image are combined, the first image being obtained by imaging the space by a camera, the second image representing the at least one type of object existing in the space and reflecting a position of the at least one type of object as seen in a depth direction in the first image, and causing the display apparatus to display the composite image.

According to an aspect, the present disclosure provides a computer-executable program for controlling a system, the system including a display apparatus and a sensor including a light source that emits irradiation light toward at least one type of object in a space and a photodetector that detects return light returning from the at least one type of object, the sensor outputting data representing a result of the detection of the return light by the photodetector, the program causing a computer to execute acquiring the data from the sensor, generating three-dimensional coordinate data representing a position, in the space, of the at least one type of object based on the data, based on the three-dimensional coordinate data; generating a composite image in which a first image and a second image are combined, the first image being obtained by imaging the space by a camera, the second image representing the at least one type of object existing in the space and reflecting a position of the at least one type of object as seen in a depth direction in the first image, and causing the display apparatus to display the composite image.

In the present disclosure, all or part of circuits, units, apparatuses, and elements, and all or part of functional blocks illustrated in the figures may be implemented by one or more electronic circuits including a semiconductor device, a semiconductor integrated circuit (IC), or an LSI (Large Scale Integration). The LSI or the IC may be integrated on a single chip or may be realized by a combination of two or more chips. For example, functional blocks other than storage elements may be integrated on a single chip. Note that the LSIs or ICs are called differently, depending on the integration density, such as a system LSI, a VLSI (Very Large Scale Integration), or a ULSI (Ultra Large Scale Integration). A field programmable gate array (FPGA) capable of being programmed after the LIS is produced, and a reconfigurable logic device capable of being reconfigured in terms of internal connections or capable of being set up in terms of internal circuits segments may also be used for the same purpose.

Part or all of functions or operations of circuits, units, apparatuses, elements may be realized by performing a software process. In this case, software may be stored in a non-transitory storage medium. The non-transitory storage medium may be one of or a combination of a ROM, an optical disk, a hard disk drive, or the like. When the software is executed by a processing apparatus (a processor), a specific function is realized by the processing apparatus (the processor) and a peripheral device. The system or the apparatus may include one or more non-transitory storage media in which software is stored, a processor, and a hardware device such as an interface.

Specific embodiments are described below with reference to drawings.

Note that any embodiment described below is provided to illustrate a general or specific example. That is, in the following embodiments of the present disclosure, values, shapes, materials, constituent elements, locations of the constituent elements and manners of connecting the constituent elements, steps, the order of steps, and the like are described by way of example but not limitation. Among constituent elements described in the following embodiments, those constituent elements that are not described in independent claims are optional.

Note that each drawing is a schematic diagram, which does not necessarily provide a strict description. For example, scales or the like are not always consistent among drawings. Also note that, in drawings, substantially the same elements are denoted by the same reference numerals, and redundant descriptions of such elements are omitted or simplified descriptions are provided.

EMBODIMENTS

Overview

A non-contact sensing system according to an embodiment captures an image of a space and detects an object existing in the space in a non-contact manner. The non-contact sensing system displays, on a display screen, a composite image in which a first image obtained by imaging a space and a second image representing a detected object are combined. In the second image, the position of the detected object as seen in the depth direction in the first image is reflected.

First, the space to which the non-contact sensing system according to the present embodiment is applied is described with reference to FIG. 1. FIG. 1 is a top view showing the space 95 to which the non-contact sensing system according to the present embodiment is applied.

The space 95 is, for example, a room in a building such as a house, an office, a nursing facility, or hospital. By way of example but not limitation, the space 95 may be a closed space partitioned by walls, a window, a door, a floor, a ceiling and/or the like, but the space 95 may be an open space outside. Alternatively, the space 95 may be an internal space of a mobile body such as a bus or an airplane.

As shown in FIG. 1, a first object 90 to be detected by the non-contact sensing system exists in the space 95. Moe specifically, the first object 90 is aerosol floating in the space 95. Examples of the aerosol include dust, suspended particulate matter such as PM2.5, biological particles such as pollen, or water microdroplets. Examples of biological particles include molds or mites floating in the air. Examples of aerosol may include a substance that is dynamically generated from a human body, such as a substance generated when coughing or sneezing occurs. Still other examples of aerosol may include a substance which is a gas component in the air such as carbon dioxide ($CO_2$) to be detected.

The object to be detected is not limited to aerosol. For example, the object may be organic dirt. Examples of organic dirt include foods or vomit stuck to an object such as a wall, a floor, or furniture existing in the space 95, which may not be suspended in the air.

2. Configuration

Figure 2:
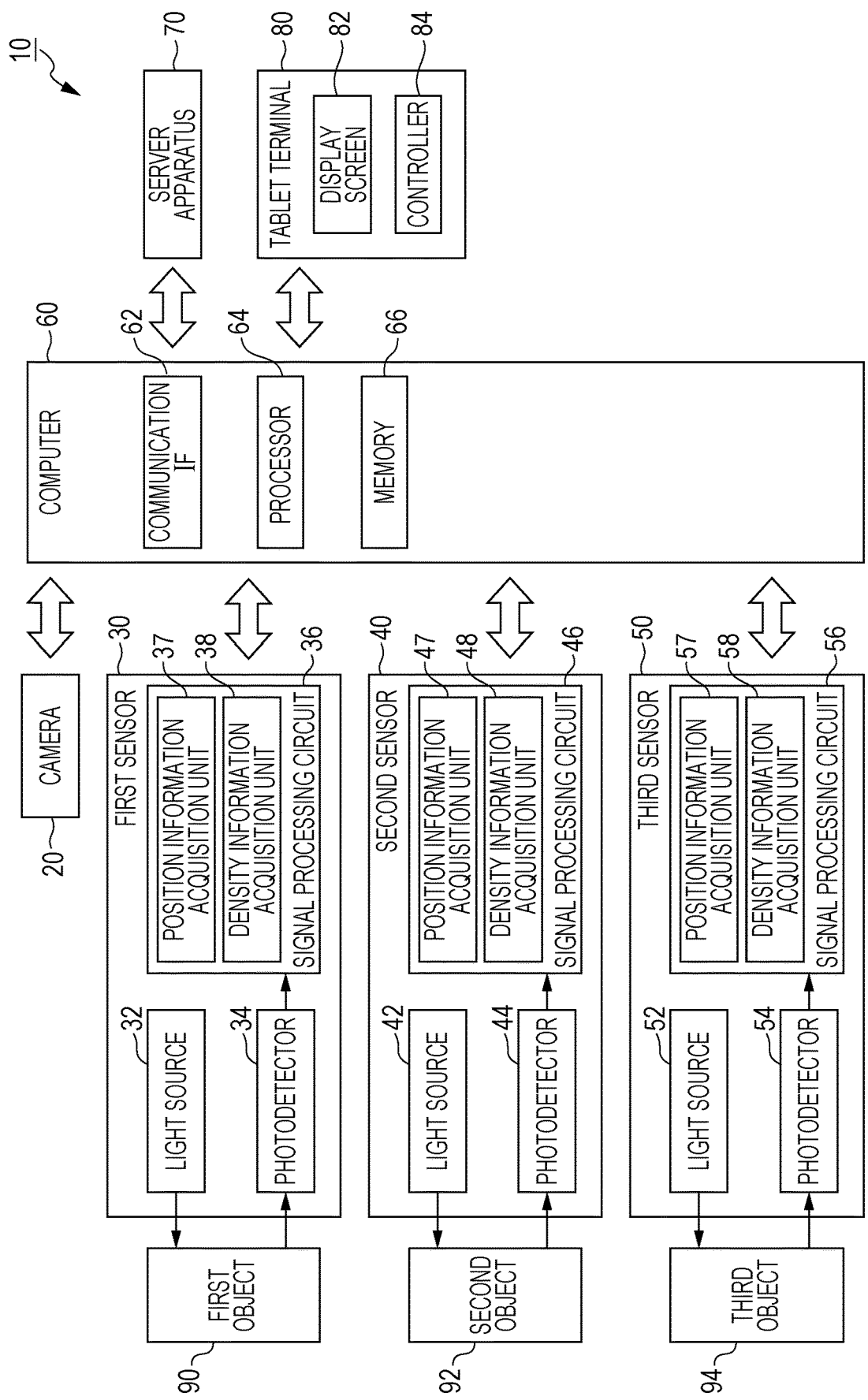
FIG. 2 is a block diagram showing a configuration of a non-contact sensing system according to an embodiment.

FIG. 2 is a block diagram illustrating a configuration of the non-contact sensing system 10 according to an embodiment. As shown in FIG. 2, the non-contact sensing system 10 includes a camera 20, a first sensor 30, a second sensor 40, a third sensor 50, a computer 60, a server apparatus 70, and a tablet terminal 80.

The configuration of the non-contact sensing system 10 is not limited to the example shown in FIG. 2. For example, the non-contact sensing system 10 may be configured so as to include only one of the first sensor 30, the second sensor 40, and the third sensor 50. That is, the number of sensor apparatuses included in the non-contact sensing system 10 may be only one, or may be two or more. The non-contact sensing system 10 may not include the computer 60 and the server apparatus 70. The non-contact sensing system 10 may include, instead of the tablet terminal 80, a display connected to the computer 60.

Although not shown in FIG. 2, the camera 20, the first sensor 30, the second sensor 40, the third sensor, the server apparatus 70, and the tablet terminal 80 each include a communication interface such that various kinds of data and information are allowed to be transmitted and received via the communication interface.

The details of the constituent elements of the non-contact sensing system 10 are described below with reference to FIG. 2.

2.1 Camera

The camera 20 captures an image of the space 95 thereby generating a captured image. The captured image is an example of the first image generated by the camera 20 by imaging the space 95. The camera 20 may be, for example, a fixed-point camera fixed at a position that allows it for the camera 20 to image the space 95. However, the camera 20 is not limited to the fixed-point type. For example, the camera 20 may be a movable camera which is movable in terms of at least one of a shooting position and a shooting direction. The camera 20 may generate two or more captured images by imaging the space 95 from two or more viewpoints. The camera 20 transmits the captured image data obtained by capturing the image to the computer 60. The camera 20 may be a visible light camera that captures an image of a space visible to humans.

2.2 Sensor Apparatus

The first sensor 30, the second sensor 40, and the third sensor 50 are each an example of the sensor apparatus that contactlessly detects an object to be detected. That is, the non-contact sensing system 10 according to the present embodiment includes three sensor apparatuses for respectively detecting particular types of objects. For example, the first object 90 shown in FIG. 2 is pollen, which is detected by the first sensor 30. The second object 92 is dust, which is detected by the second sensor 40. The third object 94 is an organic dirt, which is detected by the third sensor 50. Each of the first sensor 30, the second sensor 40, and the third sensor 50 is a non-contact sensor apparatus using, for example, LIDAR (Laser Imaging Detection and Ranging).

Figure 3:
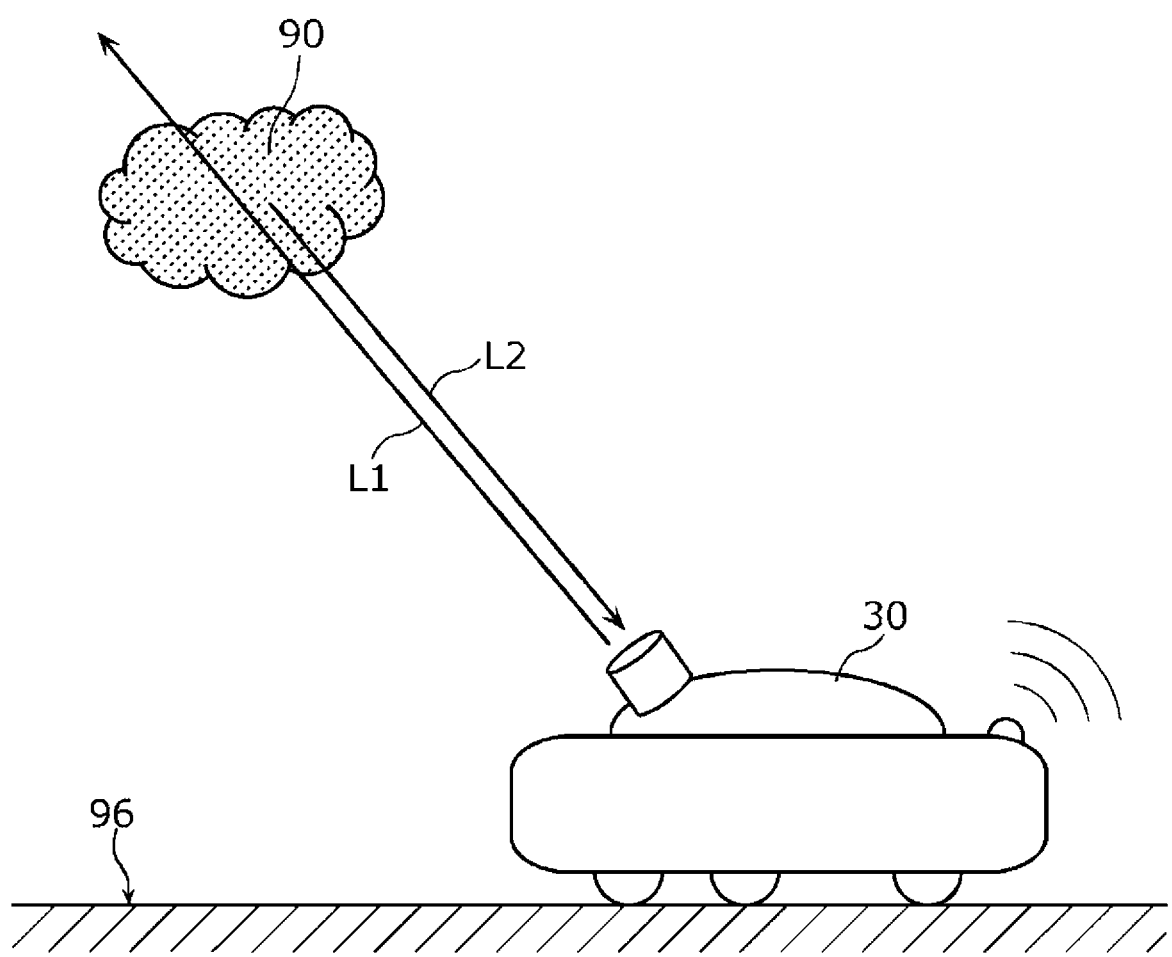
FIG. 3 is a diagram showing an example of a sensor apparatus according to an embodiment.

FIG. 3 is a diagram showing the first sensor 30, which is an example of the sensor apparatus according to the present embodiment. In the present embodiment, the first sensor 30 is an autonomous mobile sensor apparatus. Note that the second sensor 40 and the third sensor 50 each have the same configuration as that of the first sensor 30.

As shown in FIG. 3, the first sensor 30 is capable of moving on a floor surface 96 in the space 95. The first sensor 30 emits irradiation light L1 at a predetermined position on the floor surface 96 and detects return light L2 returning from the first object 90. The first sensor 30 measures the distance to the first object 90 based on a time difference between a time pf the emission of the irradiation light L1 and a time of the detection of the return light L2. The first sensor 30 also measures the density of the first object 90 based on the intensity of the return light L2.

More specifically, as shown in FIG. 2, the first sensor 30 includes a light source 32, a photodetector 34, and a signal processing circuit 36.

The light source 32 is a light source that emits the irradiation light L1 toward the first object 90 in the space 95. The light source 32 may be, for example, an LED (Light Emitting Diode) or a laser device. The irradiation light L1 emitted by the light source 32 has a wavelength component for exciting the first object 90. More specifically, the irradiation light L1 may be light having a peak wavelength in a range from a wavelength equal to or larger than 220 nm to a wavelength equal to or smaller than 550 nm. The irradiation light L1 may be, for example, pulsed light.

The photodetector 34 is a photodetector that detects the return light L2 returning from the first object 90. The return light L2 detected by the photodetector 34 is fluorescent light emitted by the first object 90 when it is excited by the irradiation light L1 emitted from the light source 32. The fluorescent light contains more long-wavelength components than the irradiation light L1 contains. The photodetector 34 may be, for example, a photodiode sensitive to the wavelength components of the fluorescent light. The photodetector 34 outputs an output signal corresponding to the intensity of the received fluorescent light to the signal processing circuit 36. The output signal is, for example, an electric signal whose signal strength increases as the intensity of the received fluorescent light increases.

The signal processing circuit 36 determines the distance to the first object 90 and the density of the first object 90 by processing the output signal output from the photodetector 34. As shown in FIG. 2, the signal processing circuit 36 includes a position information acquisition unit 37 and a density information acquisition unit 38.

The position information acquisition unit 37 acquires position information indicating a three-dimensional position of the first object 90 in the space 95. The position information includes information indicating the distance to the first object 90 and information indicating the direction thereto. For example, the position information acquisition unit 37 calculates the distance by a TOF (Time Of Flight) method. More specifically, the position information acquisition unit 37 acquires distance information based on the time difference between the time of the emission of the irradiation light L1 from the light source 32 and the time of the detection of fluorescent light by the photodetector 34. The distance information includes information indicating the distance ri to the first object 90 and information indicating the direction, represented by the horizontal angle φi and the vertical angle θi, in which the first object 90 is detected. Note that the direction in which the first object 90 is detected is the same as the direction in which the light source 32 emits the irradiation light L1.

The density information acquisition unit 38 acquires density information indicating the density of the first object 90. More specifically, the density information acquisition unit 38 determines the density of the first object 90 according to the signal strength of the output signal. For example, when the signal strength is denoted as Si, the density Di is calculated according to formula (1) shown below.

$$Di = \alpha \times Si \quad (1)$$

In formula (1), $\alpha$ is a constant, subscript "i" of each of Di, Si, ri, φi, and θi indicates the data number of the sensor data. Note that the method of calculating the density Di by the density information acquisition unit 38 is not limited to the example described above. For example, the density information acquisition unit 38 may use a signal obtained after removing noise components from the original output signal instead of the original output signal.

The signal processing circuit 36 may determine the type of the first object 90 by analyzing the fluorescent light. More specifically, the signal processing circuit 36 may determine the type of the first object 90 based on a combination of the wavelength of the irradiation light and the wavelength of the fluorescent light. For example, in the first sensor 30, the light source 32 may emit two or more irradiation light beams corresponding to two or more excitation wavelengths, and the photodetector 34 may detect two or more pieces of fluorescent light corresponding to two or more received light wavelengths. To accurately determine the type of the first object 90 that generates fluorescent light, the signal processing circuit 36 may generate a so-called fluorescence fingerprint in the form of a three-dimensional matrix of the excitation wavelength, the received light wavelength, and the received light intensity.

The signal processing circuit 36 outputs the density information indicating the determined density Di and the position information to the computer 60 as sensor data.

The first sensor 30 and the computer 60 are, for example, wirelessly connected such that data can be transmitted and received between them. The first sensor 30 performs wireless communication according to a wireless communication standard such as Wi-Fi (registered trademark), Bluetooth (registered trademark), or ZigBee (registered trademark). The connection between the first sensor 30 and the computer 60 may be realized via a wire.

The second sensor 40 emits irradiation light toward the second object 92 and detects return light returning from the second object 92 thereby detecting the second object 92. In the present embodiment, the second object is a substance that does not emit fluorescent light. An example of the second object is dust.

The second sensor 40 includes a light source 42, a photodetector 44, and a signal processing circuit 46. The light source 42, the photodetector 44, and the signal processing circuit 46 respectively correspond to the light source 32, the photodetector 34, and the signal processing circuit 36 in the first sensor 30.

The light source 42 is a light source that emits irradiation light toward the second object 92. The light source 42 may be, for example, an LED or a laser device. The irradiation light emitted by the light source 42 does not need to excite the second object 92. Therefore, the irradiation light is allowed to have a wavelength component selected from a wide wavelength band. More specifically, the irradiation light emitted from the light source 42 may be light having a peak wavelength in a range from a value equal to or greater than 300 nm to a value equal to or smaller than 1300 nm. That is, the irradiation light may be ultraviolet light, visible light, or near infrared light. The irradiation light may be, for example, pulsed light.

The photodetector 44 is a photodetector that detects return light L2 returning from the second object 92. The return light detected by the photodetector 44 is backscattered light generated when the irradiation light emitted from the light source 42 is scattered by the second object 92. For example, the backscattered light is Mie scattering light. The backscattered light has the same wavelength components as those of the irradiation light. The photodetector 44 may be, for example, a photodiode sensitive to the wavelength component of the irradiation light. The photodetector 44 outputs an output signal according to the intensity of the received backscattered light to the signal processing circuit 46. The output signal is, for example, an electric signal whose signal strength increases as the intensity of the received backscattered light increases.

In the present embodiment, the irradiation light emitted by the light source 42 may include a predetermined polarization component. The signal processing circuit 46 may determine the type of the second object 92 based on a depolarization degree of the polarization component included in the return light. The polarization component is, for example, linearly polarized light, but may be circularly polarized light or elliptically polarized light. When the second object 92 is irradiated with the irradiation light including the polarization component, the backscattered light returning from the second object 92 has a depolarization degree varying depending on the shape of the second object 92.

More specifically, when the second object 92 is a cluster of spherical particles, the polarization state is retained in its backscattered light. That is, the polarization state of the backscattered light is the same as the polarization state of the irradiation light. When the second object 92 is a cluster of non-spherical particles, the plane of polarization changes depending on the shape of the particles. This makes it possible for the signal processing circuit 46 to determine the type of the second object based on the depolarization degree of the backscattered light. For example, the depolarization degree of yellow sand is about 10%, and the depolarization degree of pollen is in a range from about 1% to about 4%.

The signal processing circuit 46 determines the distance to the second object 92 and the density of the second object 92 by processing the output signal output from the photodetector 44. As shown in FIG. 2, the signal processing circuit 46 includes a position information acquisition unit 47 and a density information acquisition unit 48. Specific operations of determining the distance and the density are the same as those of the signal processing circuit 36 of the first sensor 30.

The third sensor 50 emits irradiation light toward the third object 94 and detects return light returning from the third object 94 thereby detecting the third object 94. In the present embodiment, the third object 94 is an organic dirt that emits fluorescent light when irradiated with excitation light.

The third sensor 50 includes a light source 52, a photodetector 54, and a signal processing circuit 56. The signal processing circuit 56 includes a position information acquisition unit 57 and a density information acquisition unit 58.

The light source 52, the photodetector 54, and the signal processing circuit 56 respectively correspond to the light source 32, the photodetector 34, and the signal processing circuit 36 of the first sensor 30. The first sensor 30 and the third sensor 50 are different from each other in directions in which the respective light sources emit the irradiation light. More specifically, the light source 32 emits the irradiation light toward the air in the space 95, while the light source 52 emits the irradiation light toward the floor surface or the wall surface of the space 95. The operations of the light source 52, the photodetector 54, and the signal processing circuit 56 are respectively the same as those of the light source 32, the photodetector 34, and the signal processing circuit 36.

The first sensor 30, the second sensor 40, and the third sensor 50 each detect an object located in the direction in which the irradiation light is emitted. In a case where there are two or more objects in the emission direction of the irradiation light, the return light returns at different times depending on the positions of the objects. Therefore, two or more objects located in the emission direction of the irradiation light are detected at a time based on the time when the return light is received. Note that in a case where there is no object in the emission direction of the irradiation light, no return light is detected. Therefore, when no return light is detected, it is determined that no object exists on the path of the irradiation light. Each of the first sensor 30, the second sensor 40, and the third sensor 50 transmits a detection result as sensor data to the computer 60.

FIG. 4 illustrates an example of a database including sensor data output from the sensor apparatus according to the present embodiment. The database shown in FIG. 4 is managed by the processor 64 of the computer 60 and stored in the memory 66.

As shown in FIG. 4, in the database, the substance name Mi, the sensor data, and the sensor reference position are associated with each other for each data number No. i. The sensor data includes data in terms of the density Di, distance ri, horizontal angle $\varphi i$, and vertical angle $\theta i$.

One data number No. i is assigned to each sensor data received by the computer 60. More specifically, for example, the processor 64 assigns the data numbers in ascending order in which the communication interface 62 receives the sensor data.

The substance name Mi is information indicating the type of the object to be detected. In the present embodiment, the types of objects correspond to the respective sensor apparatuses. Therefore, the processor 64 can determine the substance name Mi corresponding to the sensor data by determining the sender of the sensor data received via the communication interface 62. For example, in the example shown in FIG. 4, the sensor data of data number 1 is data transmitted from the first sensor 30 that detects pollen.

The density Di is a value calculated according to formula (1) described above. The signal processing circuits 36, 46, and 56 of the respective sensor apparatuses perform the calculation based on the signal strength Si.

The distance ri, the horizontal angle $\varphi i$, and the vertical angle $\theta i$ indicate the three-dimensional position of the object obtained by using LIDAR. The position data obtained by LIDAR is represented in the polar coordinate system, and thus, in the present embodiment, the computer 60 performs a coordinate conversion on the position data into the three-dimensional orthogonal coordinate system. Details of the coordinate conversion will be described later.

The sensor reference position is, for example, the installation position of the sensor apparatus that is one of the first sensor 30, the second sensor 40, and the third sensor 50 and that has transmitted the sensor data. In a case where the sensor apparatus is fixed, the sensor reference position does not change. In a case where the sensor apparatus is movable, the sensor reference position is the position of the sensor apparatus at the time when the detection process is performed, and more specifically, when the irradiation light is output or the return light is received. The reference directions of the horizontal angle $\varphi i$ and the vertical angle $\theta i$ transmitted by the respective sensors, that is, the directions in which $\varphi i=0$ and $\theta i=0$, are set in advance in the same directions among the sensors.

2.3 Computer

The computer 60 is an example of the image processing apparatus, and includes the communication interface 62, the processor 64, and the memory 66, as shown in FIG. 2.

The communication interface 62 transmits and receives data in communicating with each device included in the non-contact sensing system 10. The communication with each device may be performed wirelessly based on a wireless communication standard such as Wi-Fi (registered trademark), Bluetooth (registered trademark), or ZigBee (registered trademark), or may be performed via wire.

The communication interface 62 is an example of the acquisition circuit that acquires three-dimensional coordinate data. The communication interface 62 obtains sensor data from each of the first sensor 30, the second sensor 40, and the third sensor 50 by communicating with each of the first sensor 30, the second sensor 40, and the third sensor 50. The sensor data includes position information, which is an example of three-dimensional coordinate data representing the position of at least one type of object in the space 95. The sensor data further includes density information.

The three-dimensional coordinate data is generated using coordinates of the position of the sensor apparatus in the space 95 and a relative positional relationship between the sensor apparatus and an object calculated based on the difference between the irradiation light emission time and the return light reception time. The relative positional relationship corresponds to the distance ri shown in FIG. 4. The coordinates of the sensor apparatus in the space 95 correspond to the coordinates (x0, y0, z0) indicating the reference position shown in FIG. 4.

The communication interface 62 also acquires captured image data from the camera 20 by communicating with the camera 20. The communication interface 62 may transmit a control signal including an image capturing instruction or a sensing instruction to at least one of the camera 20, the first sensor 30, the second sensor 40, and the third sensor 50. The communication interface 62 further communicates with the server apparatus 70 to transmit level distribution information corresponding to the density distribution of the object to the server apparatus 70. The communication interface 62 communicates with the tablet terminal 80 to transmit composite image data to the tablet terminal 80.

The processor 64 generates a composite image based on the sensor data acquired via the communication interface 62. The composite image is an image obtained by combining a captured image representing the space 95 captured by the camera 20 and an object image. The object image is an example of the second image representing at least one type of object existing in the space 95.

In the present embodiment, the processor 64 generates the density distribution of the object in the space 95 based on the sensor data. More specifically, the processor 64 generates a three-dimensional distribution of density such that the space 95 is represented by coordinates in a three-dimensional orthogonal coordinate system and a density is associated with each coordinate point. In FIG. 1, an x-axis, a y-axis and a z-axis shown are three axes of the three-dimensional orthogonal coordinate system. The x-axis and the y-axis are two axes parallel to the floor surface of the space 95, and the z-axis is an axis perpendicular to the floor surface. Note that the setting of the three axes is not limited to this example.

More specifically, the processor 64 generates a level distribution which is an example of the density distribution of the object. The level distribution is a distribution of the control level Ci determined based on the density information. In the present embodiment, the density Di is classified into two or more levels according to magnitudes. The control level Ci is given by one of level values into which the density Di indicated by the density information is classified. For example, the processor 64 determines the control level Ci according to a conditional expression shown in FIG. 5. FIG. 5 shows the conditional expression for determining the control level Ci in the non-contact sensing system 10 according to the present embodiment. The conditional expression is stored, for example, in the memory 66.

As shown in FIG. 5, the control level Ci is represented one of five levels from 1 to 5. The processor 64 determines the control level Ci based on the relationship between the density Di and the reference value Lm. The reference value Lm is, as shown in FIG. 6, a value predetermined for each type of object. FIG. 6 shows an example of a reference value database indicating a reference value for each substance. The reference value database is stored, for example, in the memory 66. The number of levels of the control level Ci is not limited to 5, but it may be 2, 3, or 4, or may be 6 or greater. In the conditional expression shown in FIG. 5, the value of the coefficient (for example, "0.4") by which the reference value Lm is multiplied is merely an example.

In the present embodiment, processor 64 further determines a contour of an object based on the generated three-dimensional distribution. Furthermore, the processor 64 determines a particular position inside the determined contour as a representative position. The object image includes the determined contour and the representative position.

For example, the processor 64 determines the contour of the object based on the densities Di at respective coordinate points. More specifically, the processor 64 determines the contour of the aerosol existing in the space 95 based on the control level Ci calculated based on the densities Di at the respective coordinate points.

Figures 7, 8:
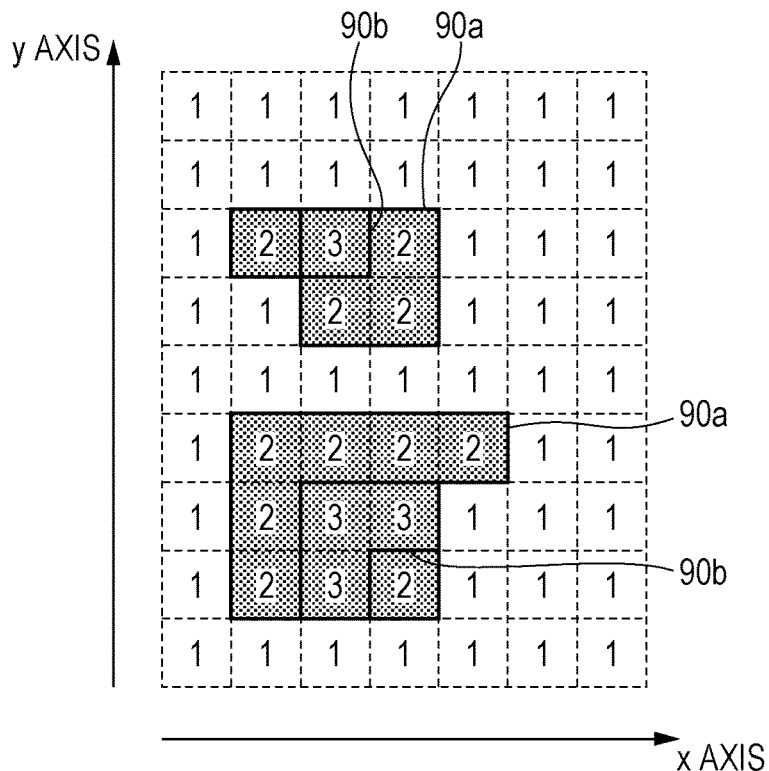
FIG. 7 is a diagram for explaining a method of determining a contour of aerosol by a non-contact sensing system according to an embodiment.
FIG. 8 is a diagram showing a representative value of a control level for each object in a space obtained by a non-contact sensing system according to an embodiment.

Referring to FIG. 7, an example of a method is described below for determining a contour of aerosol by the non-contact sensing system 10 according to the present embodiment. In the example of the method shown in FIG. 7, for simplification, a contour is determined within a two-dimensional level distribution in a plane defined by the x-axis and the y-axis. Note that a contour of a three-dimensional level distribution can also be determined in a similar manner.

As shown in FIG. 7, the control level Ci is calculated for each coordinate set of an x-coordinate and a y-coordinate. For example, the processor 64 determines a region in which the control level Ci is equal to or higher than a set value, and determines a contour of this region as the contour of the aerosol. For example, in a case where the set value is "2", the processor 64 determines a contour 90a of a region where the control level Ci is equal to or higher than "2" as the contour of the aerosol. Note that, in FIG. 7, areas where the control level Ci is equal to or higher than "2" are shaded with dots. In the example shown in FIG. 7, aerosols is detected at two locations in the space.

Note that the set value for determining the contour may be variable. For example, when the set value is increased, an area where the aerosol density is higher is determined as a region where aerosol exists. Alternatively, when the set value is reduced, a region where the aerosol density is higher than a level lower than a level indicated by the current set value is determined as a region where aerosol exists.

Note that the processor 64 may use two or more setting values in determining the contour such that contours are determined for the respective setting values. For example, in the example shown in FIG. 7, a contour 90a corresponding to a setting value of "2" while a contour 90b corresponding to a setting value of "3" are determined. The contour 90a is the outermost contour among the determined contours, and indicates the existence boundary of the aerosol. The contour 90b is a contour indicating a region where the density of the aerosol is higher in the region where aerosol exists. As described above, the density difference of the aerosol can be represented by the contours in the region where the aerosol exists.

The representative position of an area inside a contour is given by a center of gravity of an aerosol density distribution inside the counter. More specifically, the processor 64 determines the center of gravity based on the control level Ci for each of coordinate sets inside the contour. For example, when the coordinates of the center of gravity is denoted by (Xc, Yc, Zc), the processor 64 determines the coordinates of the center of gravity according to the following formula (2).

$$Xc = \Sigma(Di \times Xi)/\Sigma(Di)$$

$$Yc = \Sigma(Di \times Yi)/\Sigma(Di)$$

$$Zc = \Sigma(Di \times Zi)/\Sigma(Di) \quad (2)$$

In formula (2), $\Sigma(\ )$ is an arithmetic symbol representing the sum of terms in ( ), and i corresponds to a coordinate point located within the area surrounded by the determined contour.

The representative position may be the center of gravity of a three-dimensional graphical figure having the determined contour on the outer circumference.

The memory 66 is a storage apparatus for storing captured image data and sensor data. The memory 66 also stores a program executed by the processor 64 and parameters used in executing the program, and the like. The memory 66 also serves as a program execution area for use by the processor 64. The memory 66 may include, for example, a nonvolatile memory such as an HDD (Hard Disk Drive) or a semiconductor memory, and a volatile memory such as a RAM (Random Access Memory).

2.4 Server Apparatus

The server apparatus 70 receives the level distribution information transmitted from the computer 60 and performs a process using the received level distribution information. More specifically, the server apparatus 70 warns a person who uses the space 95 based on the level distribution information. For example, the server apparatus 70 generates a warning image which is an image for warning, and transmits the generated warning image to the tablet terminal 80.

For example, the server apparatus 70 determines whether or not the detected density of at least one type of object is greater than a threshold value, More specifically, the server apparatus 70 determines whether or not the representative control level C in the space 95 is higher than a threshold value. When the server apparatus 70 determines that the representative control level C is higher than the threshold value, the server apparatus 70 generates a warning image. The threshold value is by way of example but not limitation a predetermined fixed value. For example, the threshold value may be appropriately updated by machine learning.

The representative control level C is calculated, for example, based on the representative value Cm of the control level for each object. The representative value Cm is a value representing the control level of the corresponding object, and is given by, for example, the maximum value of the control levels in the level distribution of the corresponding object. The server apparatus 70 calculates the representative value Cm for each object based on the level distribution.

FIG. 8 shows a representative value Cm of the control level for each object in the space 95 obtained by the non-contact sensing system 10 according to the present embodiment. The server apparatus 70 calculates the representative control level C by averaging the representative values of the objects. For example, in the example shown in FIG. 8, the representative control level C is "3.8".

Note that the representative control level C may not be given by the average value of the representative values Cm. For example, the representative control level C may be a sum of weighted representative values Cm. For example, when the weight is 1 for pollen and dust, the weights for $CO_2$, water, and surface organic dirt may be 0.3, 0.1, and 0.1, respectively. The values of the weights are not limited to these values. The weights may be changeable based on an instruction given by a user or the like.

Furthermore, the server apparatus 70 may control an air conditioner installed in the space 95. The server apparatus 70 may give preventive advice for suppressing an increase in the density pollen, dust, or the like. The preventive advice is, for example, an instruction to prompt a user to ventilate the space 95 or an instruction to drive a device such as an air purifier installed in the space 95. The server apparatus 70 outputs image data or voice/sound data including preventive advice to the tablet terminal 80. For example, the server apparatus 70 acquires information regarding alerting or preventive advice by referring to meteorological observation data or the like. Furthermore, the server apparatus 70 may generate information regarding a warning or preventive advice by performing machine learning based on a temporal change in the density or the control level.

2.5 Tablet Terminal

The tablet terminal 80 is a portable information processing terminal. The tablet terminal 80 may be a multifunctional information terminal such as a tablet PC or a smartphone, or may be an information terminal dedicated to the non-contact sensing system 10. As shown in FIG. 2, the tablet terminal 80 is an example of the display apparatus including a display screen 82 and a controller 84.

The display screen 82 displays a composite image. The display screen 82 is, for example, a liquid crystal display panel, but is not limited to this. For example, the display screen 82 may be an emissive display panel using an organic EL (Electroluminescence) element. The display screen 82 may be, for example, a touch panel display which is capable of accepting an input from a user.

The controller 84 performs control such that a composite image is displayed on the display screen 82. The controller 84 includes, for example, a non-volatile memory in which a program is stored, a volatile memory serving as a temporary storage area for use in executing the program, an input/output port, a processor that executes the program, and/or the like.

In the present embodiment, the controller 84 acquires composite image data transmitted from the computer 60 and displays a composite image on the display screen 82 based on the acquired composite image data. For example, the controller 84 performs control such that a composite image 100 shown in FIG. 9 is displayed on the display screen 82.

Figure 9:
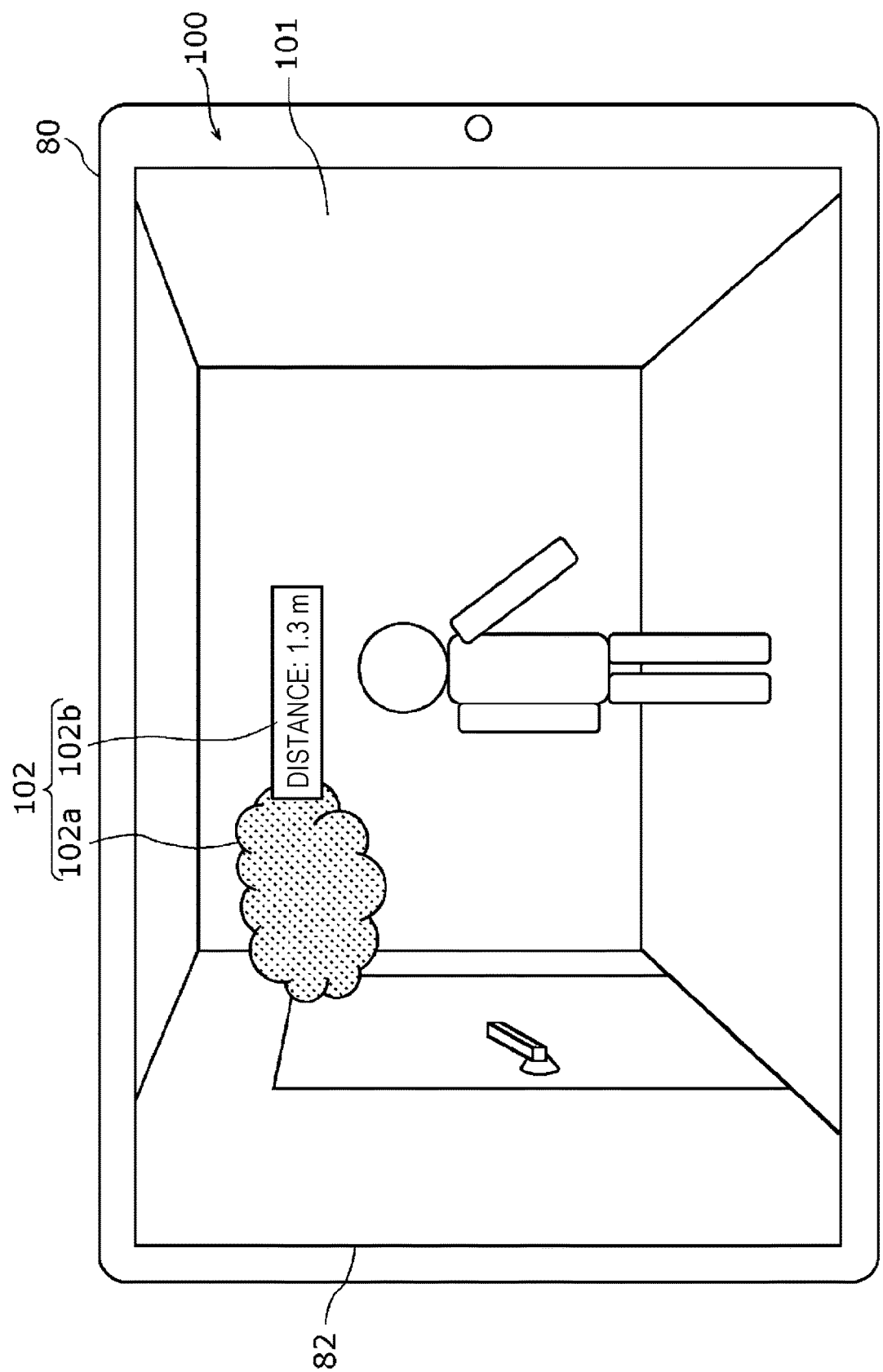
FIG. 9 is a diagram showing an example of an image displayed on a display screen of a display apparatus according to an embodiment.

FIG. 9 illustrates an example of a display image on the display screen 82 of the tablet terminal 80 which is an example of the display apparatus according to the present embodiment. As shown in FIG. 9, the composite image 100 is displayed on the display screen 82.

The composite image 100 is an image in which a captured image 101 and an aerosol image 102 are combined. The composite image 100 is, for example, a still image.

The captured image 101 represents the space 95 imaged by the camera 20. The captured image 101 is an example of the first image. The captured image 101 is obtained, by way of example but Plot limitation, by imaging the space 95 from a horizontal direction. The captured image 101 may be, for example, an image obtained by imaging the space 95 from above. In this case, the captured image 101 corresponds to the top view shown in FIG. 1.

The aerosol image 102 is an example of the object image representing at least one type of object existing in the space 95. For example, the aerosol image 102 represents pollen which is an example of aerosol. The aerosol image 102 reflects the position of at least one type of object in the depth direction in the captured image 101. The aerosol image 102 is an example of the second image.

As shown in FIG. 9, the aerosol image 102 includes a contour 102a and distance information 102b. The contour 102a represents, for example, a boundary of a region in which the first object 90 detected by the first sensor 30 exists. The distance information 102b is a numerical value indicating the distance from the reference position to the representative position in the contour 102a.

The reference position is a position defined in the space 95. For example, the reference position is the installation position of the camera 20. Alternatively, the reference position may be the position of a person or a device such as an air purifier existing in the space 95.

The aerosol image 102 may include information related to the density of the aerosol, as will be described in detail later with reference to other examples shown in FIGS. 16 to 19. More specifically, the aerosol image 102 may include level information indicating the control level Ci of the density of aerosol. In a case where two or more types of aerosol are detected, the aerosol image may represent the two or more types of aerosol in different display modes. When the density of the aerosol is higher than the threshold value, a warning image for warning a user may be displayed on the display screen 82.

3. Operation

Next, an operation of the non-contact sensing system 10 according to an embodiment is described with reference to FIGS. 10 to 15.

Figure 10:
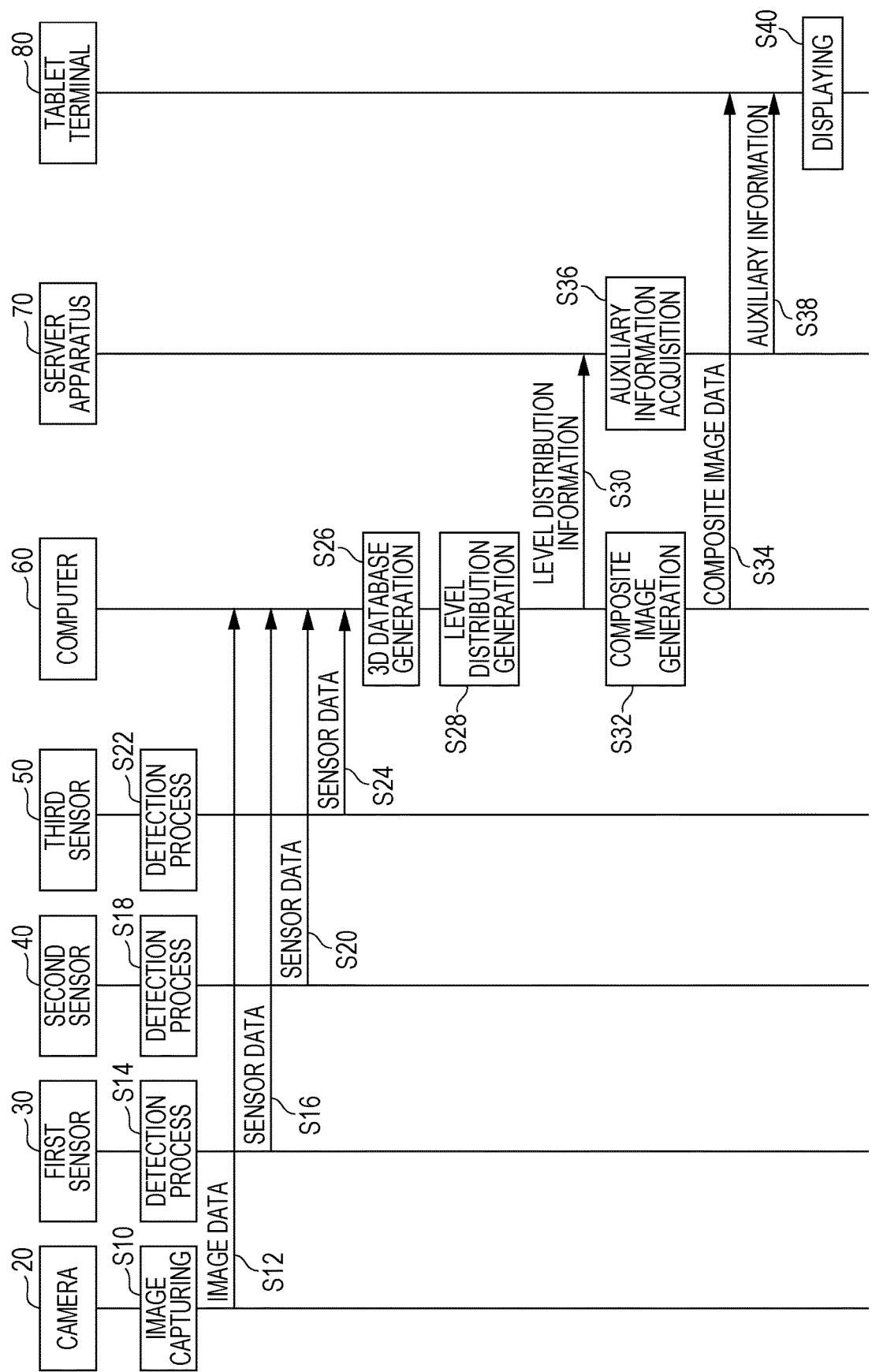
FIG. 10 is a sequence diagram showing an operation of a non-contact sensing system according to an embodiment.

FIG. 10 is a sequence diagram illustrating the operation of the non-contact sensing system 10 according to the present embodiment.

As shown in FIG. 10, first, the camera 20 images the space 95 (S10). The camera 20 transmits obtained captured image data to the computer 60 (S12).

The first sensor 30 performs a detection process for detecting the first object 90 (S14). More specifically, in the first sensor 30, the light source 32 emits irradiation light toward the first target object 90, and the photodetector 34 detects return light returning from the first target object 90. The signal processing circuit 36 generates sensor data including data indicating a distance of the first object 90 and a density of the first object 90 based on a signal strength of the return light. The first sensor 30 transmits the generated sensor data to the computer 60 (S16).

The second sensor 40 performs a detection process for detecting the second object 92 (S18). More specifically, in the second sensor 40, the light source 42 emits irradiation light toward the second object 92, and the photodetector 44 detects return light returning from the second object 92. The signal processing circuit 46 generates sensor data including data indicating a distance of the second object 92 and a density of the second object 92 based on a signal strength of the return light. The second sensor 40 transmits the generated sensor data to the computer 60 (S20).

The third sensor 50 performs a detection process for detecting the third object 94 (S22). More specifically, in the third sensor 50, the light source 52 emits irradiation light toward the third object 94, and the photodetector 54 detects return light returning from the third subject 94. The signal processing circuit 56 generates sensor data including data indicating a distance of the third object 94 and a density of the third object 94 based on a signal strength of the return light. The third sensor 50 transmits the generated sensor data to the computer 60 (S24).

Note that among the above-described processes, i.e., the image capturing (S10) by the camera 20, the detection process (S14) by the first sensor 30, the detection process (S18) by the second sensor 40, and the detection process (S22) by the third sensor 50, any one of these processes may be performed first or these processes may be performed in parallel. The image capturing (S10) and the detection processes (S14, S18, and S22) may be performed at timings based on an instruction given by the computer 60, the server apparatus 70, or the like. Each of the devices (the camera, the sensors) transmits the captured image data or the sensor data when the captured image data or the sensor data is obtained. Alternatively, each of the devices may transmit the captured image data or the sensor data when receiving a request from the computer 60.

When the computer 60 receives the captured image data and each sensor data, the computer 60 generating a 3D database based on the received captured image data and each sensor data (S26). More specifically, the processor 64 of the computer 60 converts the two-dimensional captured image into a pseudo three-dimensional image. Furthermore, the processor 64 transforms the sensor data from the polar coordinate system to a three-dimensional orthogonal coordinate system.

Figure 11:
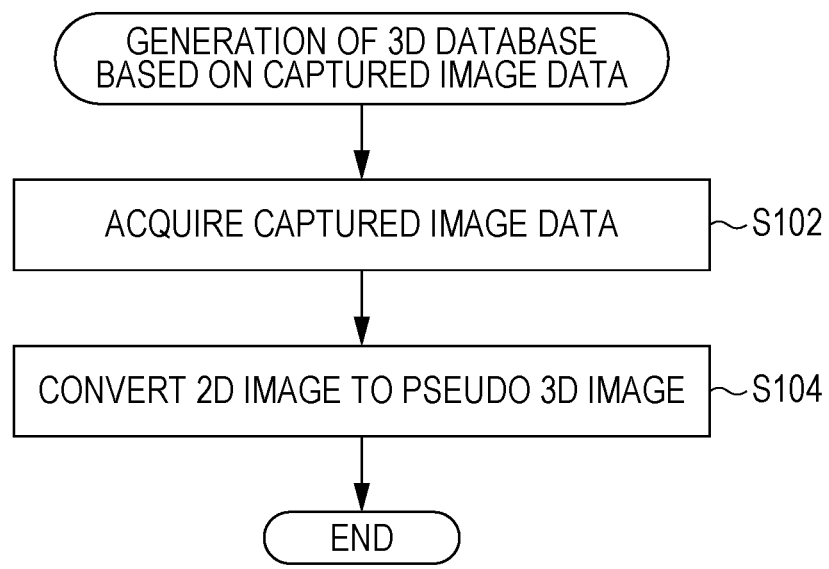
FIG. 11 is a flowchart showing an operation of converting captured image data to a 3D database, which is one of operations performed by a non contact sensing system according to an embodiment.

FIG. 11 is a flowchart showing an operation of converting captured image data to a 3D database, which is one of operations performed by the non-contact sensing system 10 according to the present embodiment. Note that FIG. 11 shows an example of a detailed operation in step S26 shown in FIG. 10.

As shown in FIG. 11, the processor 64 acquires captured image data via the communication interface 62 (S102). A captured image included in the captured image data is a two-dimensional image. The processor 64 converts the two-dimensional captured image into a pseudo three-dimensional image by using a generally known method for converting a two-dimensional image into a pseudo three-dimensional image (S104).

Note that the captured image data may include a distance image indicating distances to walls, a floor, and a ceiling that form the space 95, and distances to a person and furniture located in the space 95. The captured image data may include two or more captured images captured at different viewpoints. The processor 64 may generate a three-dimensional image by using a captured image and a distance image or by using a two or more captured images. This makes it possible to enhance the likelihood of the three-dimensional image.

Figure 12:
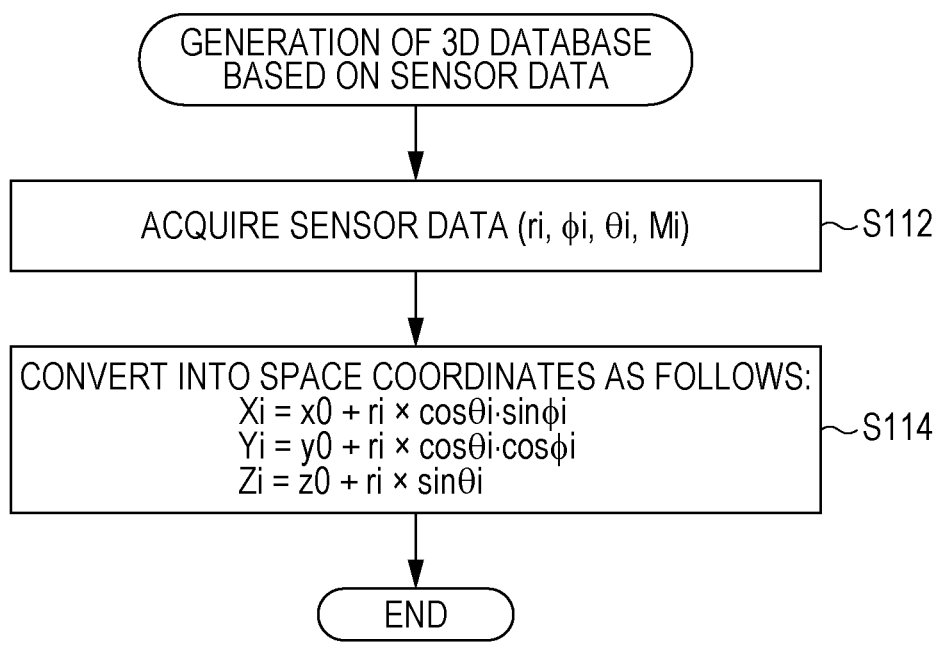
FIG. 12 is a flowchart showing an operation of converting sensor data into a 3D database, which is one of operations performed by a non-contact sensing system according to an embodiment.

FIG. 12 is a flowchart showing an operation of converting sensor data into a 3D database, which is one of operations performed by the non-contact sensing system 10 according to the present embodiment. Note that FIG. 12 shows an example of a detailed operation in step S26 shown in FIG. 10.

As shown in FIG. 12, the processor 64 acquires sensor data from the database stored in the memory 66 (S112). More specifically, the processor 64 acquires a distance $r_i$, a horizontal angle $\varphi_i$, a vertical angle $\theta_i$, and a substance name $M_i$. The processor 64 converts the acquired sensor data into spatial coordinates, that is, coordinates in a three-dimensional orthogonal coordinate system, according to a following formula (3) (S114).

$$Xi = x0 + ri \times \cos \theta i \cdot \sin \varphi i$$

$$Yi = y0 + ri \times \cos \theta i \cdot \cos \varphi i$$

$$Zi = z0 + ri \times \sin \theta i \quad (3)$$

Either of the conversion of the captured image data into the pseudo three-dimensional image shown in FIG. 11 and the conversion of the sensor data into the three-dimensional data shown in FIG. 12 may be performed first, or may be performed simultaneously. By performing the three-dimensionalization on the sensor data, the spatial coordinates (Xi, Yi, Zi) represented in the three-dimensional orthogonal coordinate system are associated with the data number No. i, as shown in FIG. 13.

FIG. 13 shows an example of a 3D database generated by the non-contact sensing system 10 according to the present embodiment. As shown in FIG. 13, a substance name Mi, a density Di, a control level Ci, and spatial coordinates (Xi, Yi, Zi) are associated with each data number No. i.

After the 3D database is generated, as shown in FIG. 10, the computer 60 generates a level distribution based on the generated 3D database (S28). The computer 60 transmits level distribution information indicating the generated level distribution to the server apparatus 70 (330).

Figure 14:
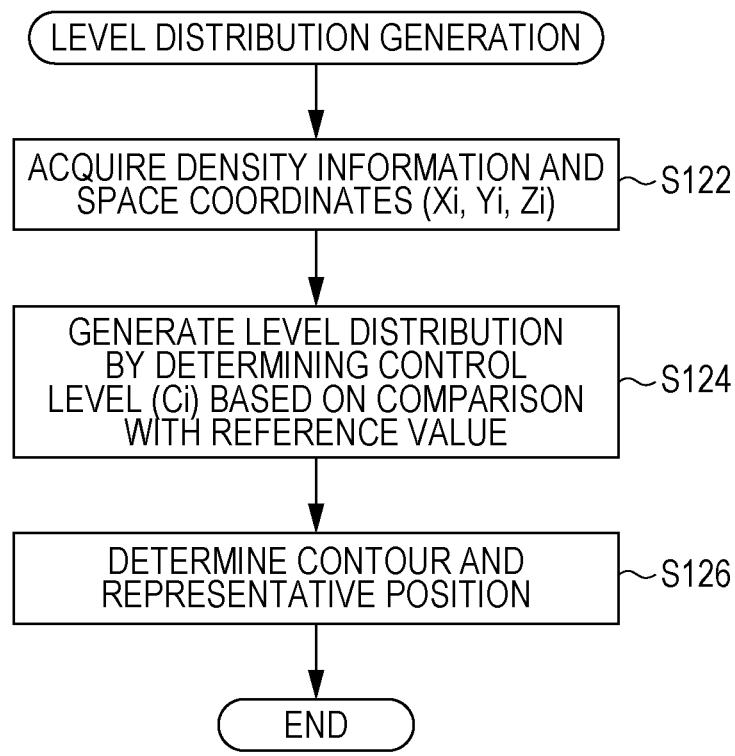
FIG. 14 is a flowchart showing an operation of generating a level distribution, which is one of operations performed by a non-contact sensing system according to an embodiment.

The process of generating the level distribution is described in further detail below with reference to FIG. 14. FIG. 14 is a flowchart showing the process of generating the level distribution, which is one of operations performed by the non-contact sensing system 10 according to the present embodiment. Note that FIG. 14 shows an example of a detailed operation in step S28 shown in FIG. 10.

As shown in FIG. 14, first, the processor 64 acquires the density information and the spatial coordinates (Xi, Yi, Zi) by reading them from the memory 66 (3122). Next, the processor 64 determines the control level Ci based on a comparison with the reference value Lm for each substance and generates the level distribution (S124). Next, the processor 64 determines a contour and a representative position in the contour based on the generated level distribution (S126). Note that the process of determining the contour and the representative position is performed in the manner described above with reference to FIG. 7.

After the level distribution is generated, the computer 60 generates a composite image as shown in FIG. 10 (S32). More specifically, the computer 60 combines the contour and the distance information with the captured image by mapping the level distribution on the captured image. The computer 60 transmits the composite image data to the tablet terminal 80 (S34).

The image including the contour and distance information is an example of the second image generated by projecting three-dimensional coordinate data representing the position in the space of at least one type of aerosol in the two-dimensional space represented by the captured image. A specific example of the image including the contour and the distance information is the aerosol image 102 shown in FIG. 9.

More specifically, the computer 60 generates the image including the contour and the distance information by projecting the three-dimensional coordinate data representing the position of at least one type of aerosol in the two-dimensional space represented by the captured image. For example, the computer 60 extends the captured image to a pseudo-three-dimensional image and performs a projection such that the extended three-dimensional image and the three-dimensional coordinate data correspond to each other, thereby generating the image including the contour and the distance information. The three-dimensional image and the three-dimensional coordinate data are made to correspond to each other by arranging the three-dimensional image and the three-dimensional coordinate data such that the origin and the three axes in the three-dimensional coordinate system in which the three-dimensional image is represented coincide with the origin and the three axes of the three-dimensional coordinate system in which the three-dimensional coordinate data are represented. The computer 60 generates a composite image by combining a captured image with an image including a contour and distance information.

The server apparatus 70 acquires auxiliary information based on the level distribution information transmitted from the computer 60 (336). The auxiliary information is, for example, information including information indicating a warning or preventive advice. The server apparatus 70 transmits the acquired auxiliary information to the tablet terminal 88 (338).

Figure 15:
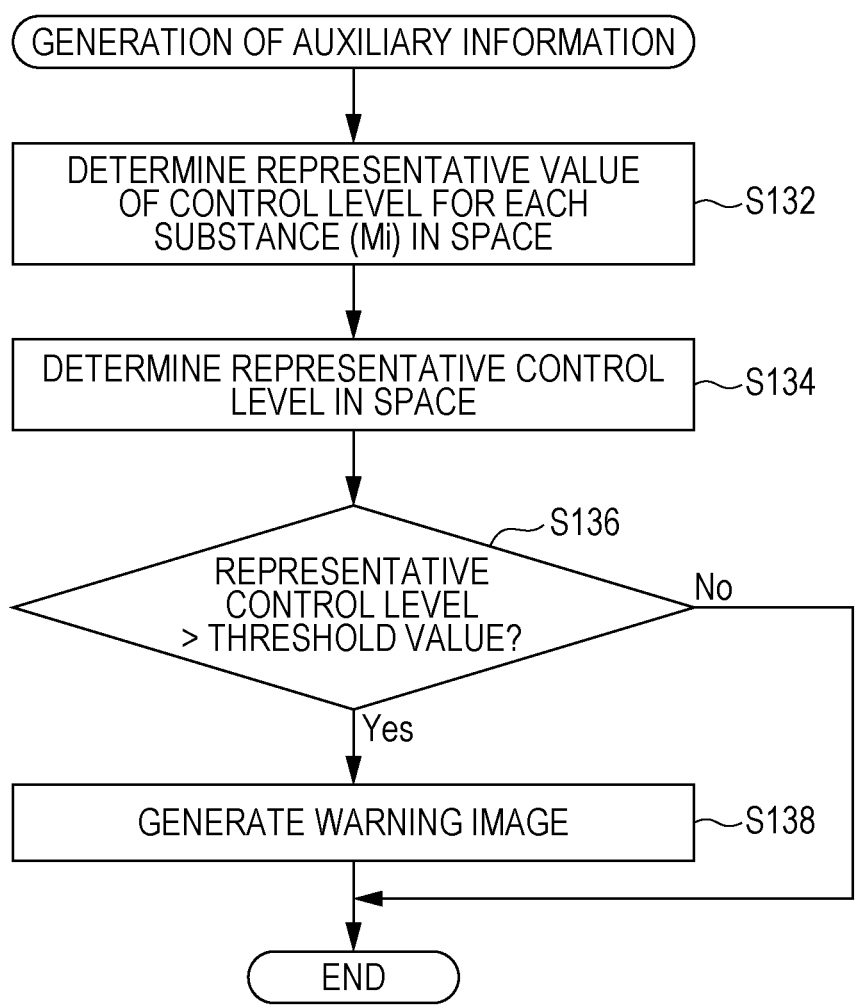
FIG. 15 is a flowchart showing an operation of generating auxiliary information, which is one of operations performed by a non-contact sensing system according to an embodiment.

Next, details of a process of generating the auxiliary information are described with reference to FIG. 15. FIG. 15 is a flowchart showing a process of generating the auxiliary information, which is one of operations performed by the non-contact sensing system 10 according to the present embodiment. Note that the process shown in FIG. 15 is an example of the detailed operation in step S36 shown in FIG. 10.

As shown in FIG. 15, first, the server apparatus 70 determines the representative value Cm of the control level for each object in the space 95 (S132). Next, the server apparatus 70 determines the representative control level C in the space 95 (S134). The specific method of determining the representative control level C is the same as described above with reference to FIG. 8.

Next, the server apparatus 70 compares the representative control level C with the threshold value (S136). When the representative control level C is higher than the threshold value (Yes in S136), the server apparatus 70 generates a warning image (S138). Instead of the warning image, preventive advice may be generated. In a case where the representative control level C is lower than or equal to the threshold value (No in S136), the auxiliary information generation process is ended.

Although the server apparatus 70 compares the representative control level C with the threshold value in the example described above, the server apparatus 70 may compare the representative value Cm of the control level for each object with the threshold value. In this case, the server apparatus 70 does not need to determine the representative control level C. For example, when at least one of the representative values Cm of the control levels of the respective objects such as pollen, dust, or the like is larger than the threshold value, the server apparatus 70 may generate a warning image.

Finally, as shown in FIG. 10, the tablet terminal 80 acquires the composite image data transmitted from the computer 60 and the auxiliary information transmitted from the server apparatus 70, and displays the composite image on the display screen 82 (S40). The composite image displayed on the display screen 82 may not include the auxiliary information. The composite image 100 shown in FIG. 9 is an example of the composite image displayed on the display screen 82. Note that in the example shown in FIG. 9, the composite image does not include auxiliary information. An example of a composite image including auxiliary information will be described later with reference to FIG. 19.

4. Other Examples of Composite Images

Specific examples of composite images displayed on the display screen 82 of the tablet terminal 80 according to the present embodiment are described below with reference to FIGS. 16 to 21. Note that in the following examples, differences from the composite image 100 shown in FIG. 9 are mainly described, and a description of common points will be omitted or simplified.

4.1 Example of Composite Image which is a Still Image (for a Case where there is Only One Type of Object)

Figure 16:
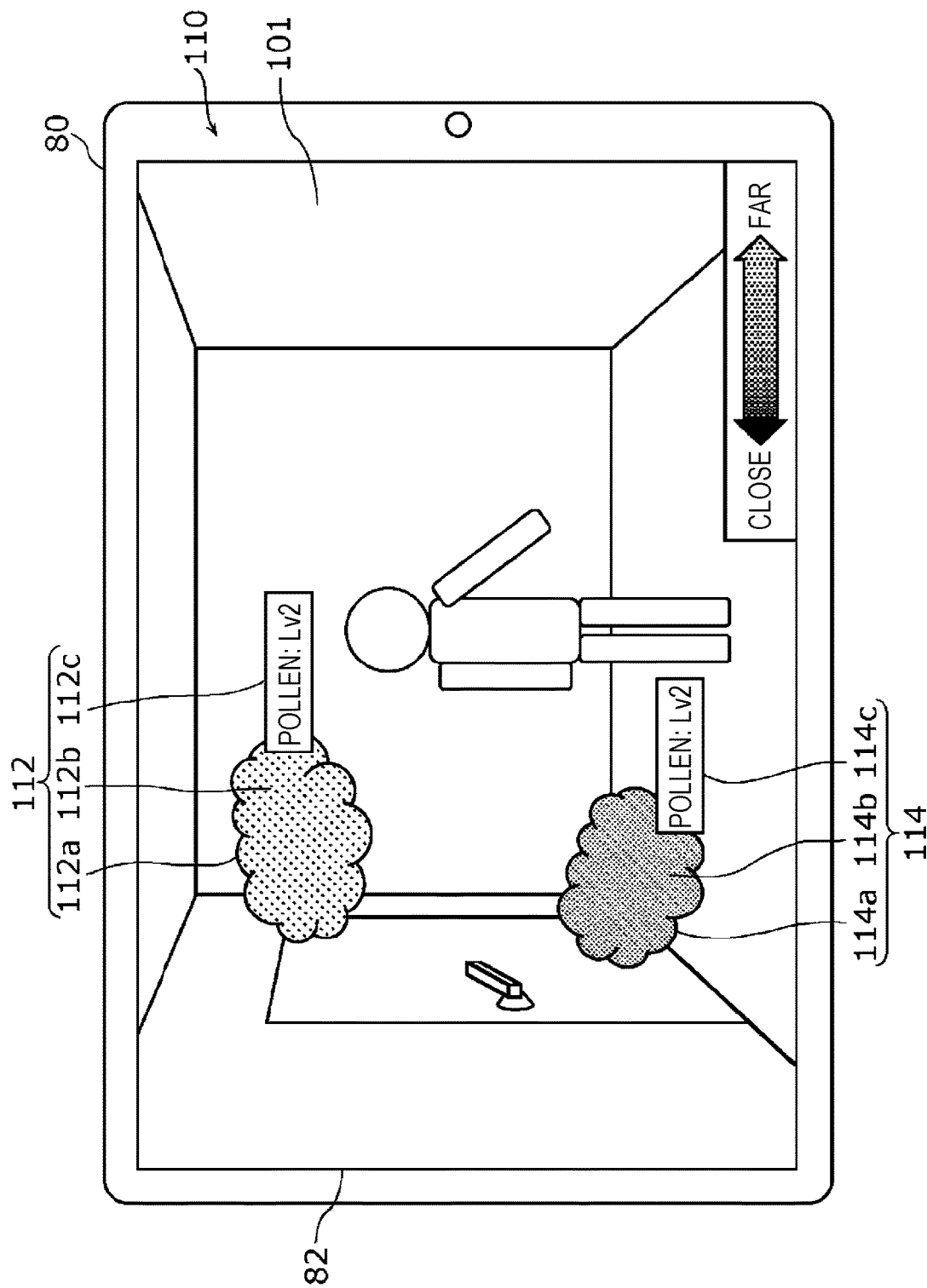
FIG. 16 is a diagram showing another example of an image displayed on a display screen of a display apparatus according to an embodiment.

FIG. 16 shows another example of a composite image displayed on the display screen 82 of the tablet terminal 80 according to the present embodiment. In this specific example shown in FIG. 16, a composite image 110 is displayed on the display screen 82.

The composite image 110 is an image obtained by combining a captured image 101 and aerosol images 112 and 114. The aerosol images 112 and 114 are each an example of a second image representing at least one type of aerosol existing in the space 95. In the example shown in FIG. 16, the aerosol images 112 and 114 each represent pollen.

As shown in FIG. 16, the aerosol image 112 includes a contour 112a and distance information 112b. Similarly, the aerosol image 114 includes a contour 114a and distance information 114b.

In the example shown in FIG. 16, the distance information 112b is a color determined depending on the distance and applied to the inside of the contour 112a. In this regard, the distance information 114b is similar to the distance information 112b. For example, a type or darkness/lightness of a color is predetermined as a function of the distance. Note that in FIG. 16, the color is represented by the density of dots inside the contour 112a. For example, the color applied inside the contour 114a as the distance information 114b is darker than the color applied inside the contour 112a as the distance information 112b. Thus, the composite image 110 indicates that the pollen represented by the aerosol image 114 is shorter in distance than the pollen represented by the aerosol image 112.

Note that the distance information 112b and 114b may be represented by densities of shades instead of colors. For example, the distance may be represented by the density of dots inside the contour 112a or 114a.

The aerosol image 112 further includes level information 112c, and the aerosol image 114 further includes level information 114c. The level information 112c indicates a type and a density of aerosol represented by the aerosol image 112. The density is represented by the level information 112c by, for example, a representative value of control levels Ci at respective coordinate points inside the contour 112a. More specifically, for example, the level information 112c indicates a maximum value or an average value of the control levels Ci at respective coordinate points inside the contour 112a. In the example shown in FIG. 16, the level information 112c includes characters representing pollen as a type of aerosol, and a numerical value representing the control level Ci. In this regard, the level information 114c indicates information in a similar manner.

As described above, in the composite image 110, the distance to the aerosol is displayed in a display mode other than a numerical value, and thus it is possible to prevent the image from including a large number of characters indicating numerical values and thus prevent the image from being complicated. The displaying of the distance in a display mode other than a numerical value allows it to use a numerical value and a character to represent the density of the aerosol. As a result, it is possible to increase the amount of information presented to a user while suppressing complication in the image.

4.2 Example of Composite Image which is a Still Image (for a Case where there are Two or More Object)

Next, an example of a composite image is described for a case where two or more types of aerosols exist in the space 95.

Figure 17:
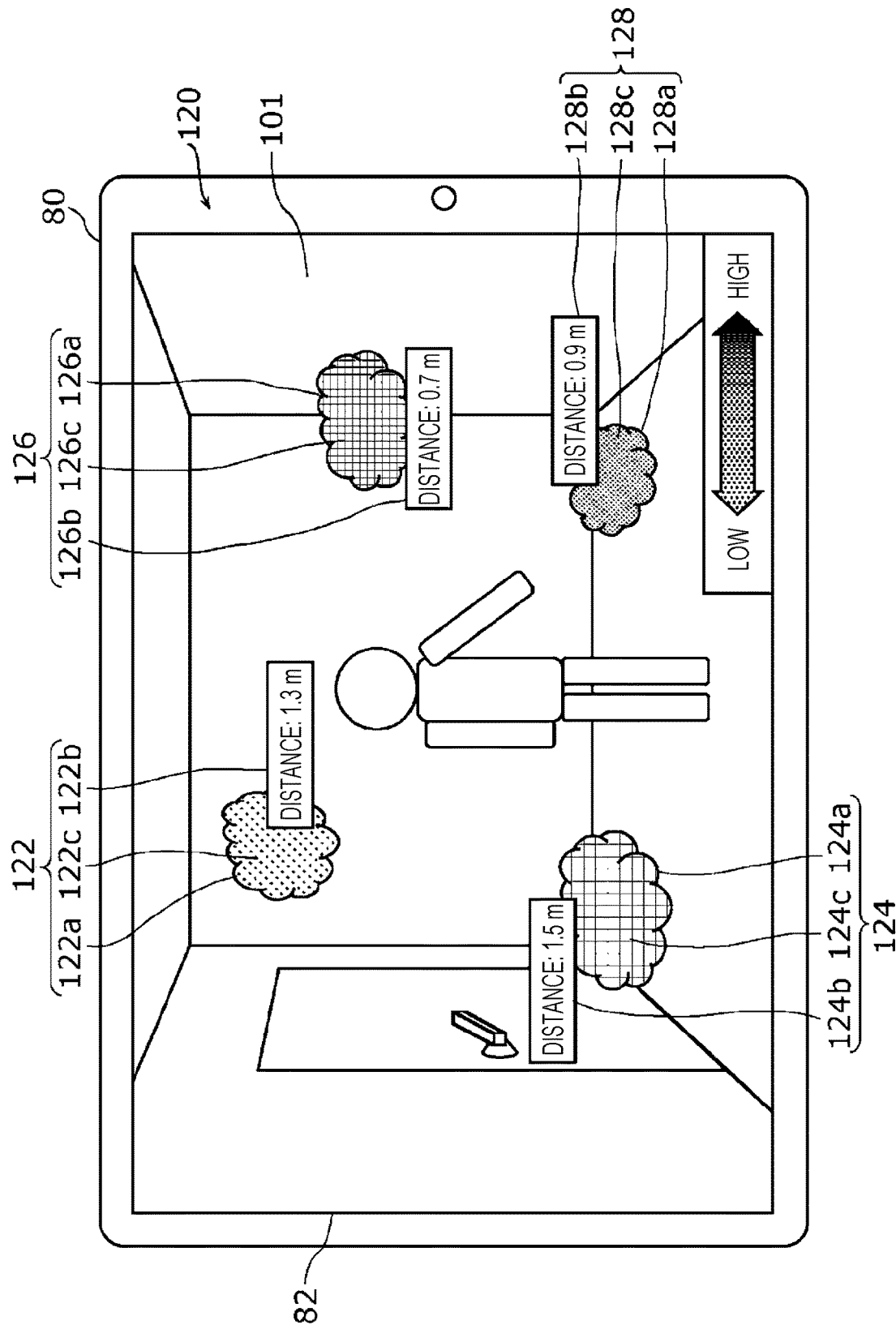
FIG. 17 is a diagram showing still another example of an image displayed on a display screen of a display apparatus according to an embodiment.

FIG. 17 shows an example of a composite image displayed on the display screen 82 of the tablet terminal 80 according to the present embodiment. That is, in FIG. 17, a composite image 120 is displayed on the display screen 82.

The composite image 120 is an image in which a captured image 101 and aerosol images 122, 124, 126, and 128 are combined. The aerosol images 122, 124, 126 and 128 each represent at least one type of aerosol existing in the space 95. In the example shown in FIG. 17, the aerosol images 122 and 128 represent pollen, and the aerosol images 124 and 126 represent dust.

As shown in FIG. 17, the aerosol image 122 includes a contour 122a and distance information 122b. The aerosol image 124 includes a contour 124a and distance information 124b. The aerosol image 126 includes a contour 126a and distance information 126b. The aerosol image 128 includes a contour 128a and distance information 128b. Each of the distance information 122b, 124b, 126b, and 128b is a numerical value indicating a distance, as in the composite image 100 shown in FIG. 9.

In the composite image 120 shown in FIG. 17, the aerosol image 122 further includes level information 122c. The aerosol image 124 further includes level information 124c. The aerosol image 126 further includes level information 126c. The aerosol image 128 further includes level information 128c.

The level information 122c is a color or a shade applied to the inside of the contour 122a. More specifically, the level information 122c represents the magnitude of the control level Ci by darkness/lightness of a color or a density of shades. For example, the level information 122c indicates the control level Ci such that the darker the color or the denser the shade, the higher the control level Ci, while the lighter the color or the sparser the shade, the lower the control level Ci. The control level Ci is represented in a similar manner also by the level information 124c, 126c, and 128c.

Furthermore, the level information 122c represents a type of aerosol by a type of color or shade. That is, the same type of aerosol is represented by the same type of color or shade. For example, in the example shown in FIG. 17, the dot mesh represents pollen and the grid mesh represents dust. In the level information 124c, 126c, and 128c, types of aerosol are represented in a similar manner.

As can be seen from the above description, the aerosol image 122 represents the same type of aerosol as that represented by the aerosol image 128. However, in the aerosol represented in the aerosol image 122, the density is low and the distance is far compared to those of the aerosol represented in the aerosol image 128. Similarly, the aerosol image 124 represents the same type of aerosol as that represented by the aerosol image 126. However, in the aerosol represented in the aerosol image 124, the density is high and the distance is close compared to those of the aerosol represented in the aerosol image 126.

Figure 18:
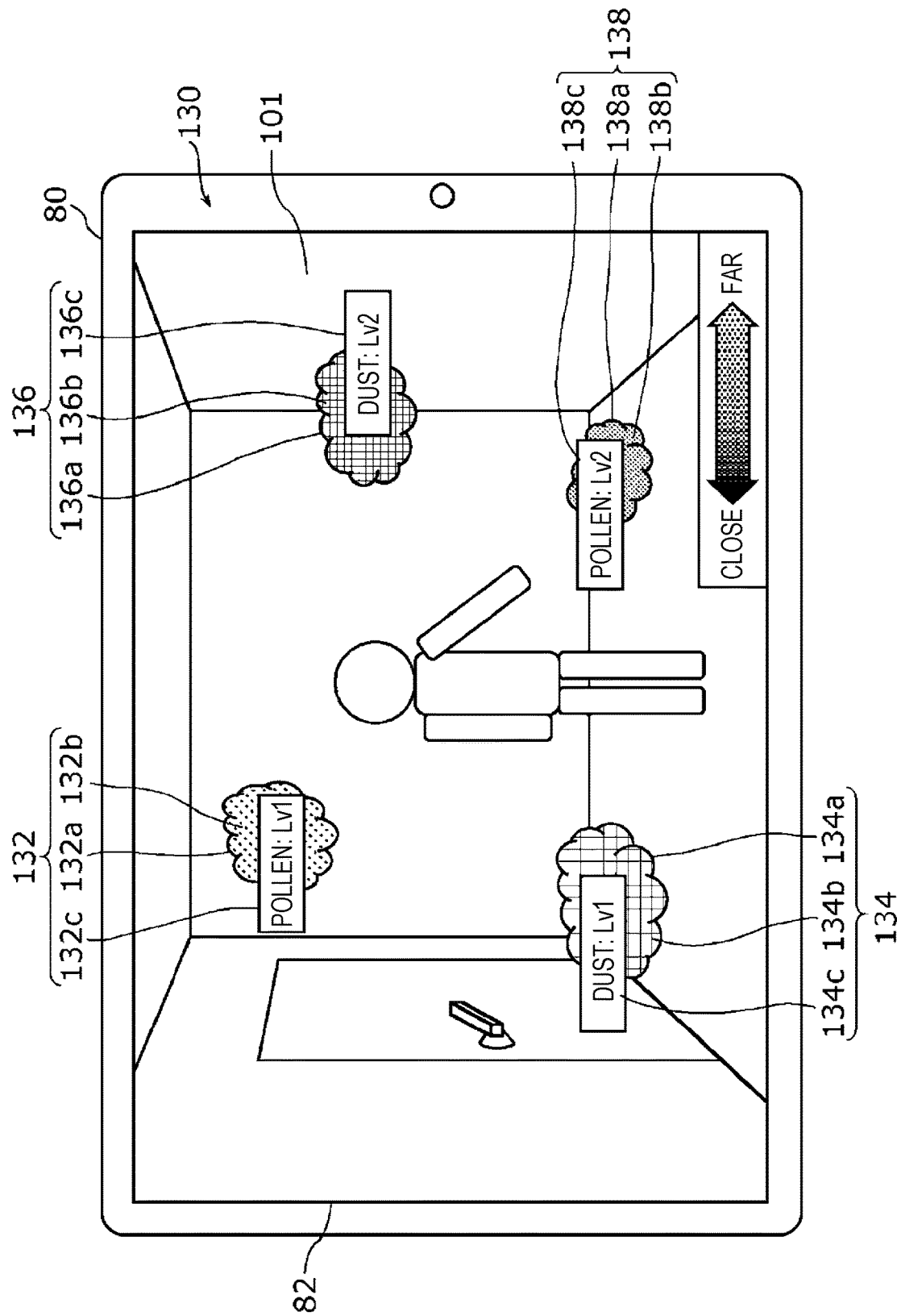
FIG. 18 is a diagram showing still another example of an image displayed on a display screen of a display apparatus according to an embodiment.

FIG. 18 shows another example of a composite image displayed on the display screen 82 of the tablet terminal 80 according to the present embodiment. As shown in FIG. 18, a composite image 130 is displayed on the display screen 82.

The composite image 130 is an image in which a captured image 101 and aerosol images 132, 134, 136, and 138 are combined. The aerosol images 132, 134, 136 and 138 each represent at least one type of aerosol existing in the space 95. In the example shown in FIG. 18, the aerosol images 132 and 138 represent pollen. The aerosol images 134 and 136 represent dust.

As shown in FIG. 18, the aerosol image 132 includes a contour 132a, distance information 132b, and level information 132c. The aerosol image 134 includes a contour 134a, distance information 134b, and level information 134c. The aerosol image 136 includes a contour 136a, distance information 136b, and level information 136c. The aerosol image 138 includes a contour 138a, distance information 138b, and level information 138c.

Each of the distance information 132b, 134b, 136b, and 138b is a color predetermined depending on the distance and applied to the inside of a contour as with the case of the composite image 110 shown in FIG. 16. In the example shown in FIG. 18, the distance information 132b, 134b, 136b, and 138b each represent a type of aerosol by a type of color or shade. That is, the same type of color or shade means the same aerosol. In the example shown in FIG. 18, a dot mesh represents pollen and a grid mesh represents dust.

Each of the level information 132c, 134c, 136c, and 138c includes characters representing pollen as a type of aerosol, and a numerical value indicating a control level Ci, as in the composite image 110 shown in FIG. 16.

As described above, types of aerosol are displayed in different display modes depending on the types, it is possible to present not only the positions of the aerosol but also the types to a user. Thus, it is possible to increase the amount of information presented to the user while suppressing complication in the image.

4.3 Example of Composite Image which is a Still Image (for a Case where the Composite Image Includes a Warning Image)

Next, an example of a composite image is described which is displayed when the density of aerosol exceeds a threshold value.

Figure 19:
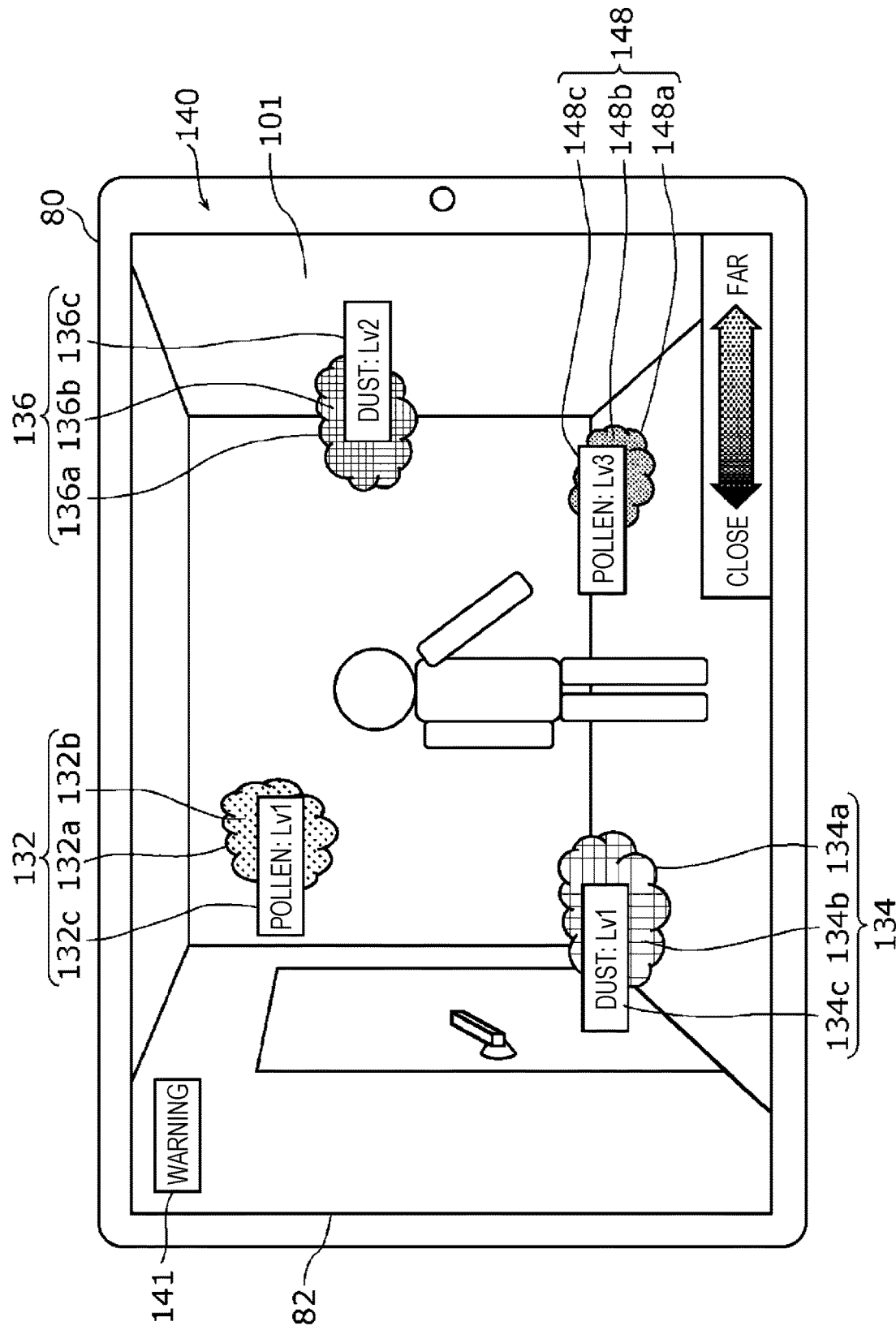
FIG. 19 is a diagram showing still another example of an image displayed on a display screen of a display apparatus according to an embodiment.

FIG. 19 shows an example of a composite image displayed on the display screen 82 of the tablet terminal 80 according to the present embodiment. As shown in FIG. 19, a composite image 140 is displayed on the display screen 82.

The composite image 140 has an aerosol image 148 instead of the aerosol image 138 included in composite image 130 shown in FIG. 18. The aerosol image 148 includes a contour 148a, distance information 148b, and level information 148c. A contour 148a, distance information 148b, and level information 148c are similar to the contour 138a, the distance information 138b, and the level information 138c shown in FIG. 18.

The level information 148c of the aerosol image 148 indicates that the control level Ci is "3". Since the control level Ci exceeds the threshold value, a warning image 141 to provide a warning is displayed on the display screen 82.

The warning image 141 may be, by way of example but not limitation, a character that provides a warning. The warning image 141 may be, for example, a particular graphical figure or the like. The mode of displaying the warning image 141 is not particularly limited as long as it can attract a user's attention. For example, the entire composite image 140 displayed on the display screen 82 may be displayed in a blinking manner, or the color tone may be changed.

In addition to the warning image 141, or instead of the warning image 141, preventive advice may be displayed on the display screen 82. The preventive advice may be displayed, for example, as character information. Alternatively, instead of the character information representing the preventive advice, a URL (Uniform Resource Locator) or a QR code (registered trademark) for connecting to a web page in which details of the preventive advice are described may be displayed.

4.4 Pseudo Three-Dimensional Image

Figure 20:
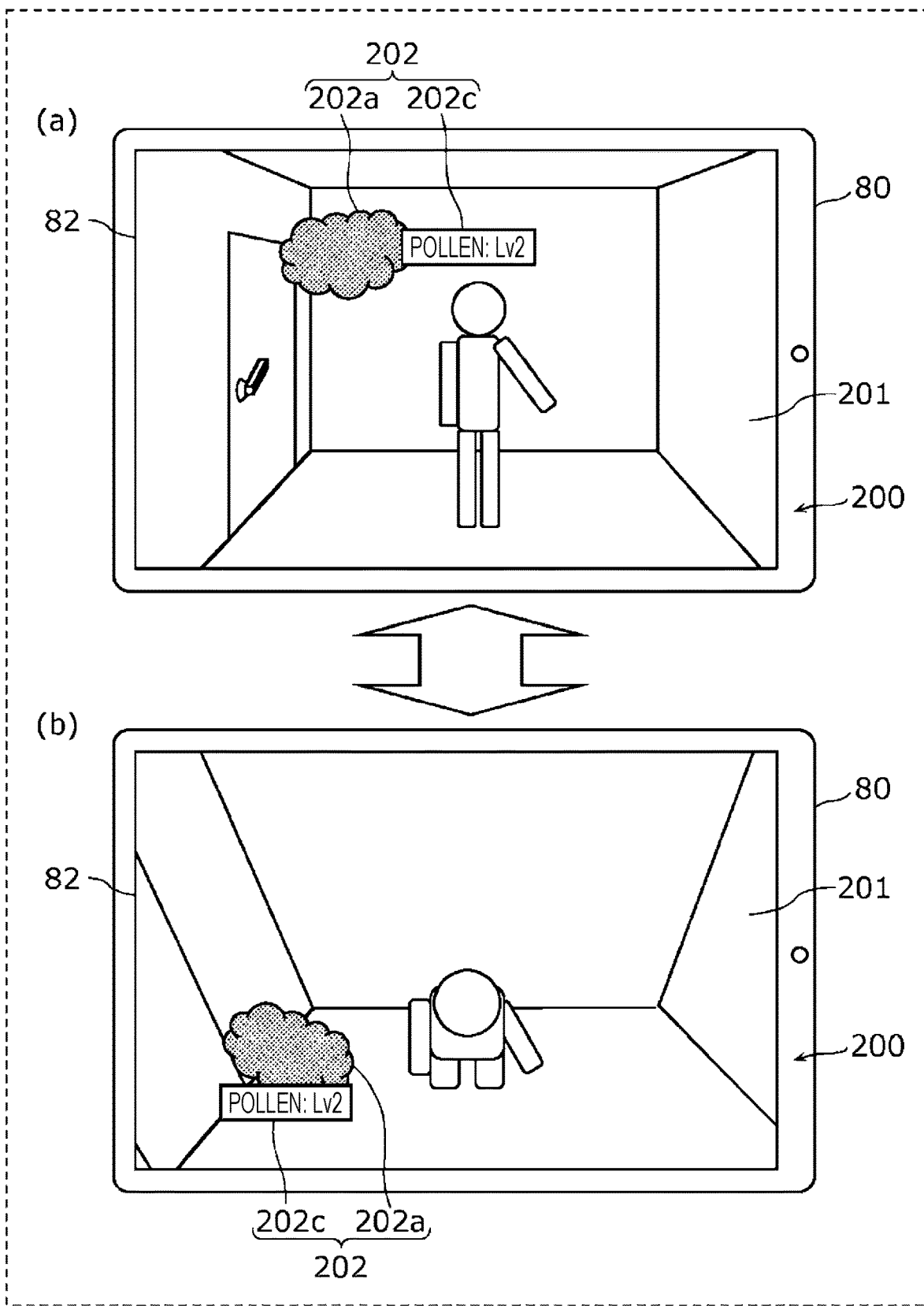
FIG. 20 is a diagram showing still another example of an image displayed on a display screen of a display apparatus according to an embodiment.

Next, an example is described below for a case where a composite image is a pseudo three-dimensional image, FIG. 20 shows an example of a composite image displayed on the display screen 82 of the tablet terminal 80 according to the present embodiment. As shown in FIG. 20, a composite image 200 is displayed on the display screen 82.

The composite image 200 is a three-dimensionally modeled image in which the space 95 and a contour representing a boundary of a region in which at least one type of aerosol exists are represented. More specifically, the composite image 200 is a pseudo three-dimensional image whose viewpoint can be changed.

As shown in FIG. 20, the composite image 200 is an image in which a captured image 201 and an aerosol image 202 are combined. The aerosol image 202 includes a contour 202a and level information 202c.

In part (a) of FIG. 20, the composite image 200 is displayed on the display screen 82 so as to show a view of the space 95 seen in a horizontal direction, as in FIG. 9. According to an instruction issued by a user or as time passes, the composite image 200 is displayed on the display screen 82 so as to show a view of the space seen obliquely from above, as shown in part (b) of FIG. 20. A user is allowed to freely change the viewpoint, for example, by swiping the display screen 82. The composite image 200 may be displayed such that it is allowed to freely enlarge or reduce the composite image.

When the viewpoint is changed, the position and the shape of the contour 202a of the aerosol image 202 are correspondingly changed. This allows it to accurately present the position of the aerosol in the space 95.

4.3 Moving Image

Next, a composite image representing aerosol is described for a case where the composite image is a moving image.

Figure 21:
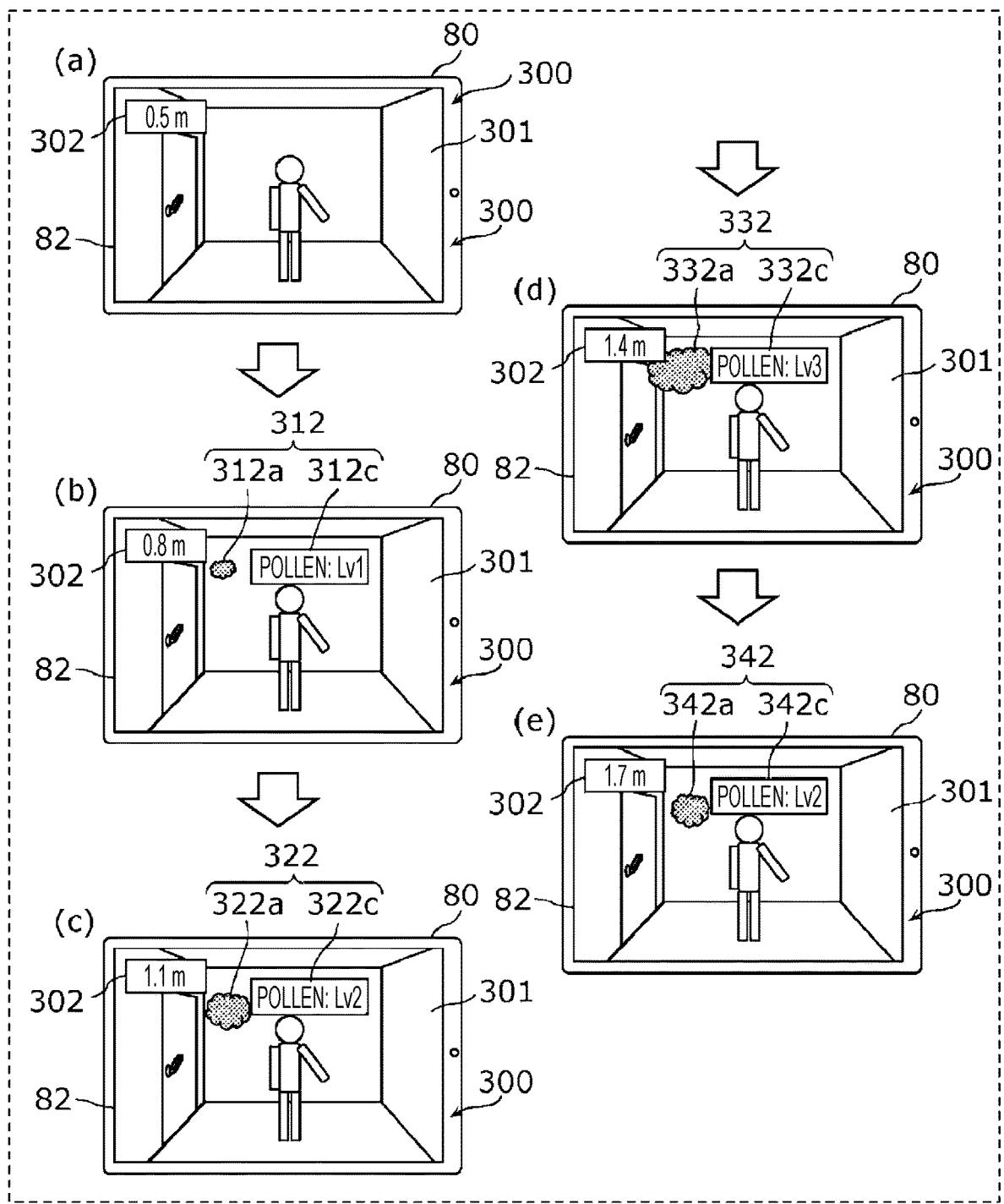
FIG. 21 is a diagram showing still another example of an image displayed on a display screen of a display apparatus according to an embodiment.

FIG. 21 shows an example of a composite image displayed on the display screen 82 of the tablet terminal 80 according to the present embodiment. As time passes, the content of the composite image displayed on the display screen 82 changes as illustrated in part (a) of FIG. 21 to part (e) of FIG. 21. The content of the composite image 300 displayed on the display screen 82 is sequentially switched at intervals of, for example, 1 second to several seconds.

The composite image 300 is an image in which a captured image 301 and aerosol images 312, 322, 332, and 342 are combined. The aerosol images 312, 322, 332 and 342 correspond to distance from the reference position.

As shown in FIG. 21, distance information 302 is displayed on the display screen 82. The distance information 302 represents the distance in the depth direction by a numerical value. The aerosol images 312, 322, 332 and 342 represent aerosols at distances of 0.8 m, 1.1 m, 1.4 m and 1.7 m, respectively.

As shown in part (a) of FIG. 21, no aerosol image is included in the composite image 300 when the distance is 0.5 m. That is, there is no aerosol at a distance of 0.5 m.

The aerosol image 312 includes a contour 312a and level information 312c. The aerosol image 322 includes a contour 322a and level information 322c. The aerosol image 332 includes a contour 332a and level information 332c. The aerosol image 342 includes a contour 342a and level information 342c.

Contours 312a, 322a, 332a, and 342a respectively represent boundaries of regions in which aerosol existing at corresponding distances. Similarly, level information 312c, 322c, 332c, and 342c represent the densities of the aerosol at the corresponding distances. More specifically, for example, the level information 312c, 322c, 332c and 342c represents the maximum values of the densities of coordinates points inside the contours of the aerosol at the corresponding distances. As shown in part (d) of FIG. 21, the aerosol has a highest control level Ci, that is, a highest density, when the distance is 1.4 m.

In the composite image 300, the captured image 301 is a still image, but it may change with time. That is, the captured image 301 may be a moving image.

OTHER EMBODIMENTS

The display apparatus, the image processing apparatus, and the control method according to one or more aspects have been described above with reference to embodiments. However, the present disclosure is not limited to those embodiments. It will be apparent to those skilled in the art that many various modifications may be applicable to the embodiments without departing from the spirit and scope of the present disclosure. Furthermore, constituent elements of different embodiments may be combined. Any such resultant modifications also falls within the scope of the present disclosure.

For example, in the above-described embodiments, it is assumed by way of example, the first sensor 30, the second sensor 40, and the third sensor 50 are each an autonomous mobile sensor. However, the sensors are not limited to those of the autonomous mobile type. At least one of the first sensor 30, the second sensor 40, and the third sensor 50 may be a stationary sensor apparatus fixed at a particular position in the space 95. The particular position is, for example, on a ceiling, a floor, or a wall of the space 95.

For example, to reflect the density on an image representing an aerosol or another object, a numerical of the density may be displayed instead of the control level. To indicate types of aerosol such that types are displayed in different modes depending on the types, line type of contours may be varied depending on the types of aerosol. For example, pollen may be represented by a solid contour line and dust may be represented by a dashed contour line.

For example, the non-contact sensing system 10 may not include the camera 20. A captured image may be obtained in advance by imaging the space 95 and may be stored in the memory 66 of the computer 60.

For example, at least one of the first sensor 30, the second sensor 40, and the third sensor 50 may be a contact sensor.

The communication method between apparatuses in the above-described embodiments is not particularly limited. When wireless communication is performed between apparatuses, a wireless communication method (a communication standard) may be, for example, ZigBee (registered trademark), Bluetooth (registered trademark), or a short-distance wireless communication such as wireless LAN (Local Area Network). Alternatively, the wireless communication method (the communication standard) may be that performed via a wide area communication network such as the Internet. Instead of wireless communication, wired communication may be performed between apparatuses. More specifically, the wired communication may be a power line communication (PLC) or a communication using a wired LAN.

In the above-described embodiments, processes executed by a specific processing unit may be executed by another processing unit. The order of executing processes may be changed, or two or more processes may be executed in parallel. The above-described manner of allocating the constituent elements of the non-contact sensing system 10 among apparatuses is merely an example. For example, instead of allocating a constituent element to a particular apparatus, the constituent element may be allocated to another apparatus. Conversely, the non-contact sensing system 10 may be realized in a single apparatus.

FIG. 22 is a diagram showing a tablet terminal 480 integrally provided with the non-contact sensing system 10 according to an embodiment. The tablet terminal 480 is a plate-shaped device. Part (a) of FIG. 22 and part (b) of FIG. 22 are plan views showing one surface and the other surface of the tablet terminal 480.

As shown in part (a) of FIG. 22, a display screen 482 is provided on a surface of one side of the tablet terminal 480. As shown in part (b) of FIG. 22, a camera 20, a light source 32, and a photodetector 34 are provided on a surface of the other side of the tablet terminal 480. Although not shown in FIG. 22, the tablet terminal 480 includes a processor 64 and a memory 66 of a computer 60 according to an embodiment. As described above, in the tablet terminal 480, the display screen 482 that displays the composite image 481 may be integrated with the camera 20, the sensor apparatus, and the computer 60.

For example, a process performed by the server apparatus 70 may be performed by the computer 60 or the tablet terminal 80. A process performed by the computer 60 may be performed by the server apparatus 70 or the tablet terminal 80.

In the above-described embodiments, it is assumed by way of example that the computer 60 generates composite images. However, the controller 84 of the tablet terminal 80 may generate a composite image. More specifically, the controller 84 may perform the process, in FIG. 11, of converting the captured image data into the 3D database and the process of converting the sensor data into the 3D database. The controller 84 may perform, in FIG. 10, the conversion into 3D database (S26), the generation of the level distribution (328), and the generation of the composite image (S32).

One or more processes described in the above embodiments may be realized by performing centralized processing using a single apparatus or a system, or may be realized by performing distributed processing using two or more apparatuses. One or more programs may be executed by a single processor or two or more processors. That is, processes may be performed in the centralized manner or distributed manner.

In the above-described embodiments, all or part of the constituent elements such as the controller may be implemented by hardware or may be realized by executing software programs corresponding to the constituent elements. Each constituent element may be realized by reading a software program stored in a storage medium such as an HDD (Hard Disk Drive), a semiconductor memory, or the like and executing the software program by a program execution unit such as a CPU (Central Processing Unit), a processor, or the like.

Furthermore, the constituent elements such as the controller may be configured by one or more electronic circuits.

The one or more electronic circuits each may be a general-purpose circuit or a dedicated circuit.

The one or more electronic circuits may include, for example, a semiconductor device, an IC (Integrated Circuit), or an LSI (Large Scale Integration). The IC or LSI may be integrated on one chip or may be integrated on two or more chips. Note that the ICs or LSIs are called differently, depending on the integration density, such as a system LSI, a VLSI (Very Large Scale Integration), or a ULSI (Ultra Large Scale Integration). Furthermore, an FPGA (Field Programmable Gate Array) capable of being programmed after the LSI is produced, thereby properly may also be used for the same purpose.

General or specific embodiments may be implemented as a system, an apparatus, a method, an integrated circuit, or a computer program, or general or specific embodiments may be implemented by a computer-readable non-transitory storage medium such as an optical disk, an HDD, a semiconductor memory, or the like in which the computer program is stored. General or specific embodiments may be implemented by any selective combination of a system, an apparatus, a method, an integrated circuit, a computer program, and a storage medium.

Also note that in each embodiment described above, various changes, replacements, additions, removals, or the Ike are possible without departing from scope of the present disclosure or equivalent scope.

The present disclosure may be used as a display apparatus or the like to accurately present a precise position of aerosol, and may be used, for example, for air conditioning control or space purification processing control.

What is claimed is:

1. A display apparatus comprising:
   a display screen; and
   a controller that causes the display screen to display a composite image in which a first image acquired by imaging a space by a camera and a second image representing at least one type of aerosol existing for real in the space of the first image are combined,
   wherein the at least one type of aerosol is a particle floating in the space,
   wherein a position of the at least one type of aerosol as seen in a depth direction in the first image is reflected in the second image, and
   wherein a density of the at least one type of aerosol is further reflected in the second image, the density of the at least one type of aerosol is obtained by irradiating an incident light to the at least one type of aerosol, and an intensity of a return light from the at least one type of aerosol corresponds to the density of the at least one type of aerosol.

2. The display apparatus according to claim 1, wherein
   the first image represents a two-dimensional space,
   the controller generates the second image by projecting three-dimensional coordinate data representing the position of the at least one type of aerosol in the space onto the two-dimensional space, and
   the controller generates the composite image by combining the first image and the second image.

3. The display apparatus according to claim 2, wherein
   the controller acquires the three-dimensional coordinate data from a sensor that acquires a position of the at least one type of aerosol in the space,
   the controller converts the first image into a pseudo three-dimensional image, and
   the controller generates the second image by projecting the three-dimensional coordinate data into the two-dimensional space such that the pseudo three-dimensional image and the three-dimensional coordinate data correspond to each other.

4. The display apparatus according to claim 1, wherein the second image includes a contour representing a boundary of a region in which the at least one type of aerosol exists and distance information representing a distance in the space from a reference position to a representative position of the region inside the contour.

5. The display apparatus according to claim 4, wherein the representative position is a center of gravity of a density distribution of the at least one type of aerosol in the region inside the contour.

6. The display apparatus according to claim 4, wherein the distance information is a numerical value indicating the distance.

7. The display apparatus according to claim 4, wherein the distance information is a color that is predetermined according to the distance and is applied to the region inside the contour.

8. The display apparatus according to claim 1, wherein the composite image represents a three-dimensional model including the space and a contour representing a boundary of a region in which the at least one type of aerosol exists.

9. The display apparatus according to claim 1, wherein
   the second image is a moving image including images that are switched as time passes, and
   each of the images
   corresponds to a distance from a reference position in the space, and
   includes a contour indicating a boundary of a region, at the corresponding distance, in which the at least one type of aerosol exists.

10. The display apparatus according to claim 1, wherein the second image includes level information indicating a density level of the at least one type of aerosol.

11. The display apparatus according to claim 1, wherein
    the at least one type of aerosol includes two or more types of aerosol, and
    the second image represents the respective two or more types of aerosol in different display modes.

12. The display apparatus according to claim 1, wherein the controller further causes the display screen to display an image for warning a user in a case where the density of the at least one type of aerosol is greater than a threshold value.

13. An image processing apparatus comprising:
    an acquisition circuit that acquires three-dimensional coordinate data representing a position, in a space, of at least one type of aerosol existing for real in the space; and
    a processor, wherein
    wherein the at least one type of aerosol is a particle floating in the space,
    the processor generates a composite image in which a first image acquired by imaging the space by a camera and a second image representing the at least one type of aerosol existing for real in the space of the first image are combined based on the three-dimensional coordinate data,
    a position of the at least one type of aerosol as seen in a depth direction in the first image is reflected in the second image, and
    a density of the at least one type of aerosol is further reflected in the second image, the density of the at least one type of aerosol is obtained by irradiating an incident light to the at least one type of aerosol, and an intensity of a return light from the at least one type of aerosol corresponds to the density of the at least one type of aerosol.

14. A control method of controlling a system,
the system comprising
a sensor that includes a light source emitting irradiation light toward at least one type of object in a space and a photodetector detecting return light returning from the at least one type of object, the sensor outputting data representing a result of detection of the return light by the photodetector, and
a display apparatus,
the control method comprising:
acquiring the data from the sensor:
generating three-dimensional coordinate data representing a position, in the space, of the at least one type of object based on the data;
based on the three-dimensional coordinate data, generating a composite image in which a first image and a second image are combined, the first image being obtained by imaging the space by a camera, the second image representing the at least one type of object existing for real in the space of the first image, reflecting a position of the at least one type of object as seen in a depth direction in the first image, wherein the at least one type of object is a particle floating in the space, and reflecting a density of the at least one type of object in the second image, wherein the density of the at least one type of object is obtained by irradiating an incident light to the at least one type of object, and an intensity of a return light from the at least one type of object corresponds to the density of the at least one type of object; and
causing the display apparatus to display the composite image.

15. The control method according to claim 14, wherein
the return light is fluorescent light emitted by the at least one type of object by being excited by the irradiation light, and
the generating of the composite image includes determining a type of the at least one type of object by analyzing the fluorescent light and reflecting the type in the second image.

16. The control method according to claim 15, wherein
the irradiation light includes a polarization component, and
the generating of the composite image includes determining the type of the at least one type of object based on degree of depolarization of the polarization component included in the return light and reflecting the type in the second image.

17. The control method according to claim 14, wherein the three-dimensional coordinate data is generated using coordinates of a position of the sensor in the space and a relative positional relationship between the sensor and the at least one type of object calculated based on a difference between an irradiation light emission time and a return light reception time.

18. The control method according to claim 14, wherein the at least one type of object is an organic substance stuck to an object existing in the space.

19. The control method according to claim 14, wherein the at least one type of object is aerosol existing in the space.

20. The control method according to claim 19, wherein the return light is backscattered light generated as a result of scattering of the irradiation light by the at least one type of object.

21. A non-transitory computer-readable storage medium storing a program for controlling a system,
the system comprising
a sensor that includes a light source emitting irradiation light toward at least one type of object in a space and a photodetector detecting return light returning from the at least one type of object, the sensor outputting data representing a result of detection of the return light by the photodetector, and
a display apparatus,
the program, when executed by the computer, performing:
acquiring the data from the sensor;
generating three-dimensional coordinate data representing a position, in the space, of the at least one type of object based on the data;
based on the three-dimensional coordinate data, generating a composite image in which a first image and a second image are combined, the first image being obtained by imaging the space by a camera, the second image representing the at least one type of object existing for real in the space of the first image, reflecting a position of the at least one type of object as seen in a depth direction in the first image, wherein the at least one type of object is a particle floating in the space, and reflecting a density of the at least one type of object in the second image, wherein the density of the at least one type of object is obtained by irradiating an incident light to the at least one type of object, and an intensity of a return light from the at least one type of object corresponds to the density of the at least one type of object, and
causing the display apparatus to display the composite image.

* * * * *